US009809803B2

(12) United States Patent
Nakamura

(10) Patent No.: US 9,809,803 B2
(45) Date of Patent: Nov. 7, 2017

(54) MITOGEN-ACTIVATED PROTEIN KINASE-DEPENDENT RECOMBINANT VACCINIA VIRUS (MD-RVV) AND USE THEREOF

(71) Applicants: National University Corporation Tottori University, Tottori-shi, Tottori (JP); The Chemo-Sero-Therapeutic Research Institute, Kumamoto-shi, Kumamoto (JP)

(72) Inventor: Takafumi Nakamura, Yonago (JP)

(73) Assignees: National University Corporation Tottori University, Tottori (JP); The Chemo-Sero-Therapeutic Research Institute, Kumamoto (JP)

( * ) Notice: Subject to any disclaimer, the term of this patent is extended or adjusted under 35 U.S.C. 154(b) by 0 days.

(21) Appl. No.: 15/038,145

(22) PCT Filed: Nov. 20, 2014

(86) PCT No.: PCT/JP2014/081484

§ 371 (c)(1),
(2) Date: May 20, 2016

(87) PCT Pub. No.: WO2015/076422

PCT Pub. Date: May 28, 2015

(65) Prior Publication Data

US 2016/0281066 A1 Sep. 29, 2016

(30) Foreign Application Priority Data

Nov. 21, 2013 (JP) ................................ 2013-241299

(51) Int. Cl.
*C07D 417/00* (2006.01)
*C12N 7/00* (2006.01)
(Continued)

(52) U.S. Cl.
CPC .............. *C12N 7/00* (2013.01); *A61K 35/768* (2013.01); *A61K 48/00* (2013.01); *C12N 15/09* (2013.01);
(Continued)

(58) Field of Classification Search
CPC ........... C12N 7/00; C12N 2710/24132; C12N 2710/24162; C12N 2710/24121; A61K 48/00; A61K 35/768
See application file for complete search history.

(56) References Cited

U.S. PATENT DOCUMENTS

| | | | |
|---|---|---|---|
| 2003/0031681 | A1 | 2/2003 | McCart et al. |
| 2013/0071430 | A1 | 3/2013 | Nakamura et al. |

FOREIGN PATENT DOCUMENTS

| | | |
|---|---|---|
| WO | 2011/125469 | 10/2011 |
| WO | 2013/038066 | 3/2013 |

OTHER PUBLICATIONS

Schweneker, Marc., et al., "The Vaccinia Virus O1 Protein is Required for Sustained Activation of Extracellular Signal-Regulated Kinase 1/2 and Promotes Viral Virulence", Journal of Virology, 2012, vol. 86, No. 4, pp. 2323-2336.
(Continued)

*Primary Examiner* — Reza Ghafoorian
(74) *Attorney, Agent, or Firm* — McCarter & English, LLP

(57) ABSTRACT

This invention provides a vaccinia virus that grows specifically in a cancer cell and damages such cancer cell and the use of such virus for treatment of cancer. Such mitogen-activated protein kinase-dependent vaccinia virus strain lacks functions of vaccinia virus growth factor (VGF) and O1L, it does not grow in normal cells but grows specifically in cancer cells, and it has oncolytic properties that specifically damage cancer cells.

9 Claims, 18 Drawing Sheets
(10 of 18 Drawing Sheet(s) Filed in Color)

(51) Int. Cl.
*A61K 48/00* (2006.01)
*C12N 15/09* (2006.01)
*A61K 35/768* (2015.01)

(52) U.S. Cl.
CPC .............. *C12N 2710/24121* (2013.01); *C12N 2710/24132* (2013.01); *C12N 2710/24162* (2013.01); *C12N 2710/24171* (2013.01)

(56) References Cited

OTHER PUBLICATIONS

Buller, R. Mark, et al., "Deletion of the Vaccinia Virus Growth Factor Gene Reduces Virus Virulence", Journal of Virology, Mar. 1998, vol. 62, No. 3, pp. 866-874.
McCart, J. Andrea, et al., "Systematic Cancer Therapy with a Tumor-Selective Vaccinia Virus Mutant Lacking Thymidine Kinase and Vaccinia Growth Factor Genes", Cancer Research, Dec. 15, 2001, vol. 61, No. 24, pp. 8751-8757.
International Search Report of International Application No. PCT/JP2014/081484, dated Mar. 3, 2015.

MITOGEN-ACTIVATED PROTEIN KINASE-DEPENDENT RECOMBINANT VACCINIA VIRUS (MD-RVV) AND USE THEREOF

RELATED APPLICATIONS

This application is a national stage application filed under 35 USC 371 of PCT/JP2014/081484, filed Nov. 20, 2014, which claims the benefit of Japanese Patent Application No. 2013-241299, filed Nov. 21, 2013, all of which are incorporated herein, in entirety, by reference.

Submission of Sequence Listing

The Sequence Listing associated with this application is filed in electronic format via EFS-Web and hereby incorporated by reference into the specification in its entirety. The name of the text file containing the Sequence Listing is 11924400093.txt. The size of the text file is 8 KB, and the text file was created on May 18, 2016.

TECHNICAL FIELD

The present invention relates to a novel vaccinia virus and a virus vector utilizing such virus. More specifically, the present invention relates to a vaccinia virus, which is deprived of functions of virus proteins (i.e., a vaccinia virus growth factor (VGF) and O1L); that is, a mitogen-activated protein kinase-dependent recombinant vaccinia virus that grows specifically in a cancer cell and has oncolytic properties of destroying such cancer cell.

BACKGROUND ART

In recent years, various oncolytic virotherapy techniques involving the use of viruses for treatment of cancer have been developed. Examples of viruses used for such therapy include adenoviruses, retroviruses, and vaccinia viruses.

Because of wide host range and high expression efficiency, in recent years, vaccinia viruses have been used as polyvalent vaccines for infectious diseases (e.g., HIV and SARS) in the form of expression vectors into which foreign genes have been introduced.

In addition, a technique for treatment of cancer making use of the oncolytic properties of vaccinia viruses has been reported (see Patent Document 1).

Separately, the vaccinia virus growth factor (VGF) gene and the O1L gene have been reported as genes that activate ERK in the infected cells and positively regulate the growth of vaccinia viruses (see Non-Patent Document 1). With respect to the VGF gene, it was reported that vaccine pathogenicity would be reduced via deletion of the VGF gene (see Non-Patent Document 2). Also, use of a vaccinia virus, which is deprived of the VGF gene and the TK (thymidine kinase) gene, for treatment of cancer, has been reported (see Patent Document 2 and Non-Patent Document 3).

PRIOR ART DOCUMENTS

Patent Documents

Patent Document 1: WO 2011/125469

Patent Document 2: WO 2013/038066

Non-Patent Documents

Non-Patent Document 1: Schweneker M. et al., Journal of Virology, Vol. 86, No. 4, pp. 2323-2336, 2012

Non-Patent Document 2: Buller R M. et al., Journal of Virology, Vol. 62, No. 3, pp. 866-874, 1988

Non-Patent Document 3: McCart J A. et al., Cancer Research, Vol. 61, No. 24, pp. 8751-8757, 2001

SUMMARY OF THE INVENTION

It is an object of the present invention to provide a vaccinia virus that grows specifically in a cancer cell and damages the cancer cell and it is another object to provide the use of such virus for treatment of cancer.

To date, preclinical tests and clinical trials concerning oncolytic virotherapy aimed at treatment of cancer with the use of live viruses have been actively conducted across the globe.

In the case of vaccinia viruses, vaccinia virus growth factor (VGF) that exhibits a high degree of homology to epidermal growth factor (EGF) is produced at the initial stage of infection. Secreted VGF binds to epidermal growth factor receptor (EGFR) in the infected cells or cells located in the vicinity thereof and activates the Ras/Raf/MEK/ERK metabolic pathway, so as to promote mitosis. In recent years, the O1L, protein encoded by the vaccinia virus O1L gene has been reported to activate ERK in the infected cells. Since VGF and O1L were considered to activate the same pathway, deprivation of the functions of VGF that would act on the upstream region was considered significant, and deprivation of the functions of O1L that would act on the downstream region was considered less significant.

The present inventors presumed as follows. That is, when a protein encoded by a gene that has functions of activating ERK is deprived of its functions, mitosis is not promoted because ERK cannot be activated when the virus infects a normal cell. As a result, viral growth is significantly reduced. In cancer cells in which the Ras/Raf/MEK/ERK metabolic pathway is activated to an abnormal extent, in contrast, functions of viruses to activate ERK are complemented with abnormal activation. As a result, viruses grow, cancer cells are lysed, and pathogenicity is reduced. The present inventors conducted concentrated studies in order to verify such presumption. As a result, they discovered that safety of the viruses would be improved unexpectedly in normal cells and the oncolytic properties thereof on cancer cells would be enhanced unexpectedly via deletion of functions of both the VGF protein and the O1L protein. This has led to the completion of the present invention.

Specifically, the present invention is as described below.

[1] A mitogen-activated protein kinase-dependent vaccinia virus, which is deprived of functions of the vaccinia virus growth factor (VGF) and O1L, which does not grow in a normal cell but grows specifically in a cancer cell, and which has oncolytic properties of specifically damaging cancer cells.

[2] The mitogen-activated protein kinase-dependent vaccinia virus according to [1], wherein the vaccinia virus is the LC16 strain, the LC16mO strain, or the LC16m8 strain modified to express the B5R gene.

[3] A pharmaceutical composition used for treatment of cancer comprising the vaccinia virus according to [1] or [2].

[4] A mitogen-activated protein kinase-dependent vaccinia virus vector comprising foreign DNA introduced into the mitogen-activated protein kinase-dependent vaccinia virus according to [1] or [2].

[5] The mitogen-activated protein kinase-dependent vaccinia virus vector according to [4], wherein the foreign DNA is marker DNA, a therapeutic gene having cytotoxic effects or immunostimulating effects, or DNA encoding a cancer, virus, bacterium, or protozoan antigen.

[6] A pharmaceutical composition comprising the mitogen-activated protein kinase-dependent vaccinia virus vector according to [4] or [5], which is used for treatment of cancer or used as a vaccine against cancer, viruses, bacteria, or protozoa.

This description includes part or all of the content as disclosed in the description and/or drawings of Japanese Patent Application No. 2013-241299, which is a priority document of the present application.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

FIG. 5-1 shows viral infection and ERK activity in normal cells and tumor cells in the absence of serum.

FIG. 5-2 shows viral infection and ERK activity in normal cells and tumor cells in the presence and in the absence of serum.

FIG. 12A shows the distribution of peritoneal disseminated tumors and FIG. 12B shows tumor-specific viral growth. FIG. 12C shows the results of *Renilla* luciferase (Rluc) detection, FIG. 12D shows the results of phosphorylated p44/42 MAPK protein (Erk1/2) (pERK) detection, and FIG. 12E shows the results of vaccinia virus detection.

EMBODIMENTS FOR CARRYING OUT THE INVENTION

Hereafter, the present invention is described in detail.

The vaccinia virus according to the present invent on is a mitogen-activated protein kinase (MAPK)-dependent recombinant vaccinia virus (MD-RVV), which is deprived of functions of the vaccinia virus growth factor (VGF) and O1L.

SEQ ID NOs: 1 and 2 show the gene sequences of VGF and O1L of the vaccinia virus, respectively.

A mitogen-activated protein kinase (MAPK) is a serine/threonine kinase, and a representative example thereof is ERK. When an epidermal growth factor (EGF) binds to an epidermal growth factor receptor (EGFR), the Ras/Raf/MEK/ERK signal cascade is activated, and mitosis is promoted.

Vaccinia virus growth factor (VGF) is a protein exhibiting a high degree of amino acid sequence homology with EGF, it binds to EGFR as with EGF, it activates the signal cascade, and it promotes mitosis.

When cells are infected with vaccinia viruses, vaccinia virus growth factor (VGF) is produced at the initial stage of infection. Secreted VGF binds to epidermal growth factor receptor (EGFR) in the infected cells or cells located in the vicinity thereof and activates the Ras/Raf/MEK/ERK metabolic pathway, so as to promote mitosis. Also, O1L encoded by the vaccinia virus O1L gene activates ERK in the infected cells. Specifically, both VGF and O1L activate ERK and positively regulate the growth of vaccinia viruses.

Figure 1:
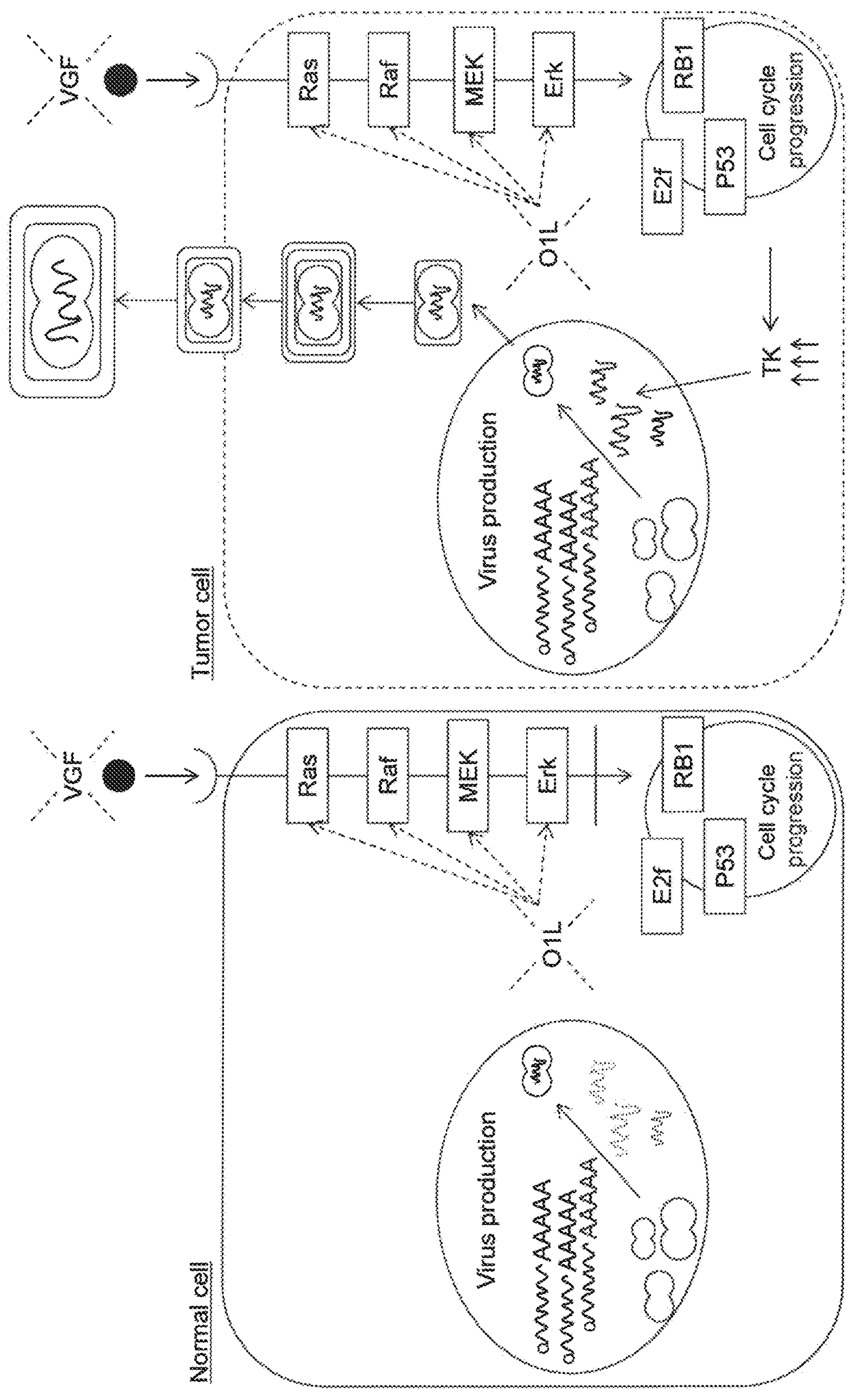
FIG. 1 shows the principles whereby a normal cell is not damaged and a cancer cell is damaged by the mitogen-activated protein kinase (MAPK)-dependent recombinant vaccinia virus.

Since both virus proteins (i.e., VGF and O1L) activate ERK and regulate the growth of vaccinia viruses, these two vaccinia virus proteins may be deprived of functions such that ERK would not be activated by VGF and O1L in the infected cells. When the Ras/Raf/MEK/ERK metabolic pathway in a normal cell is compared with that in a cancer cell, the Ras/Raf/MEK/ERK metabolic pathway is activated to an abnormal extent in a cancer cell. Even if ERK is not activated by VGF and O1L, accordingly, ERK is activated, and mitosis is promoted. When normal cells are infected with vaccinia viruses, which are deprived of functions of VGF and O1L, accordingly, ERK is not activated in normal cells. Thus, mitosis is not promoted, and, as a consequence, the growth of vaccinia viruses is reduced significantly (FIG. 1, left). In contrast, the Ras/Raf/MEK/ERK metabolic pathway is activated to an abnormal extent in cancer cells, the functions of VGF and O1L of the vaccinia viruses to activate ERK are complemented thereby, and, accordingly, the vaccinia viruses can grow (FIG. 1, right). As a result, the vaccinia viruses grow in a cancer-cell-specific manner, and they destroy and damage cancer cells. That is, the mitogen-activated protein kinase-dependent recombinant vaccinia virus according to the present invention has cancer-cell-specific oncolytic properties.

Vaccinia virus strains to be used for the production of the mitogen-activated protein kinase (MAPK)-dependent recombinant vaccinia virus according to the present invention are not limited. Examples thereof include: the Lister strain; strains established from the Lister strain, such as the LC16 strain, the LC16mO strain and the LC16m8 strain (So Hashizume, Clinical Virology, vol. 3, No. 3, 269, 1975, and others); the NYBH strain; the Wyeth strain; the Copenhagen strain; the WR strain; and the MVA strain. The LC16mO strain is produced from the LC16 strain, which is established from the Lister strain. The LC16m8 strain is an attenuated strain, which is produced from the LC16mO strain, wherein expression and function of B5R gene encoding a viral membrane protein, is hampered due to a frame-shift mutation (Protein, Nucleic Acid, Enzyme, Vol. 48, No. 12 (2003), pp. 1693-1700).

At present, preclinical tests and clinical trials concerning oncolytic virotherapy aimed at treatment of cancer with the use of live viruses have been actively conducted throughout the globe. In such virotherapy, the manner of eliminating the inherent pathogenicity of the virus against normal tissue is the most important issue of concern.

From the viewpoint of established safety when administered to a human, it is preferable that vaccinia viruses used in the present invention be attenuated and free of pathogenicity. An example of such an attenuated strain is a strain that has been partially or completely deprived of the B5R gene. The B5R gene encodes a protein existing in a vaccinia viral envelope, and the B5R gene product is associated with viral infection and growth. The B5R gene product is present on the surface of the infected cell and in the virus envelope. When viruses infect and propagate in adjacent cells or other regions within the host body, infection efficiency is enhanced, and this is associated with the plaque size and the host region of the viruses. If the B5R gene is deleted, the size of the plaque formed when an animal cell is infected is reduced, and the pock size is also reduced, in addition, the ability of viruses to grow in the skin is lowered, and the pathogenicity in the skin is lowered. In the case of the vaccinia virus that is partially or completely deprived of the B5R gene, the B5R gene product does not have its normal functions, and the growth ability in the skin is low. Even if it is administered to a human, accordingly, no side effects would occur. An example of an attenuated strain that is deprived of the B5R gene is the m8Δ strain (also referred to as the "LC16m8Δ strain") established from the LC16m8 strain by completely deleting the B5R gene. The mOΔ strain (also referred to as the "LCmOΔ" strain) established from the LC16mO strain by completely deleting the B5R gene can also be used. Such attenuated vaccinia virus strains that are partially or completely deprived of the B5R gene are disclosed in WO 2005/054451, and such strains can be obtained in accordance with the description thereof. Whether or not a vaccinia virus is partially or completely deprived of the B5R gene and lacks functions of the B5R protein can be determined with the use of, for example, the size of the plaque formed when the virus has infected the RK13 cell, the pock size, the viral growth capacity in Vero cells, or the pathogenicity in the skin of a rabbit as an indicator. Alternatively, the gene sequence of the vaccinia virus may be examined.

The vaccinia virus used in the present invention expresses the B5R gene in a cancer cell and damages the cancer cell through the action of the B5R protein. Accordingly, it is preferable that the vaccinia virus used in the present invention express the complete B5R gene. When using the attenuated vaccinia virus, the safety of which is established because of the lack of the B5R gene, a complete B5R gene is introduced into the vaccinia virus that lacks the B5R gene. When a vaccinia virus that is partially or completely deprived of the B5R gene is used, the B5R gene is inserted into the genome of the vaccinia virus, and the resultant may be used as a material for producing the vaccinia virus according to the present invention. The B5R gene may be inserted into the vaccinia virus by any means. For example, a known technique of homologous recombination may be employed. In such a case, the B5R gene may be inserted thereinto at a position between the B4R gene and the B6R gene where the B5R gene was originally present or at any position in the genome of the vaccinia virus. Alternatively, the B5R gene may be constructed in the form of a DNA construct in advance, and the resulting construct may be introduced into the vaccinia virus.

According to a technique of homologous recombination, two DNA molecules are recombined with each other via the same nucleotide sequence in a cell. Such technique is often employed for recombination of viruses having very extensive genomic DNAs, such as vaccinia viruses. At the outset, a plasmid is constructed by inserting the B5R gene into the target vaccinia virus gene in such a manner that the sequence of the vaccinia virus gene is divided in the middle thereof (with the resultant being referred to as the "transfer vector"), and the resulting plasmid is introduced into the cell infected with the vaccinia virus. As a result, recombination takes place between the virus DNA that became naked during the virus replication and the same sequence of the transfer vector, and the inserted B5R acne is incorporated into the virus genome. Examples of cells that can be infected with vaccinia viruses include BSC-1 cells, HTK-143 cells, Hep2 cells, MDCK cells, Vero cells, HeLa cells, CV1 cells, COS cells, RK13 cells, BHK-21 cells, and primary rabbit kidney cells. Vectors may be introduced into cells in accordance with conventional techniques, such as the calcium phosphate method, the cationic ribosome method, or electroporation.

Deprivation of functions of VGF and O1L of the vaccinia virus means that a gene encoding VGF and a gene encoding O1L are not expressed or the expressed proteins do not retain normal functions of VGF and O1L even if such genes are expressed. The vaccinia virus may be deprived of functions of VGF and O1L by partially or completely deleting the gene encoding VGF and the gene encoding O1L. Alternatively, genes may be mutated via substitution, deletion, or addition of nucleotides, so as to prevent normal VGF or O1L from being expressed. Alternatively, a foreign gene may be inserted into the gene encoding VGF or the gene encoding O1L. Insertion of a foreign gene or deletion or mutation of a gene can be implemented by, for example, a known technique of homologous recombination or site-directed mutagenesis. When a normal gene product is not expressed because of deletion or mutation of a gene in the present invention, a gene of interest is deleted.

Whether or not VGF and O1L lack functions may be determined by producing the mitogen-activated protein kinase-dependent recombinant vaccinia virus lacking functions of VGF and O1L according to the present invention and inspecting whether or not such virus has expressed these proteins. For example, the presence of VGF or O1L can be examined via immunological assays involving the use of an antibody reacting with VGF or an antibody reacting with O1L. Alternatively, the presence of the gene encoding VGF or the gene encoding O1L can be determined via PCR.

The mitogen-activated protein kinase-dependent vaccinia virus according to the present invention can be used for the treatment of cancer. More specifically, the present invention relates to a pharmaceutical composition used for the treatment of cancer that comprises the mitogen-activated protein kinase-dependent vaccinia virus.

Targets of cancer treatment are not limited. When types of cancer are classified in accordance with primary lesions, for example, any type of cancer, such as lung cancer, pancreatic cancer, ovarian cancer, skin cancer, gastric cancer, hepatic cancer, colon cancer, anorectal cancer, esophageal cancer, uterine cancer, breast cancer, bladder cancer, prostate cancer, esophageal cancer, cranial nerve tumor, lymphoma/leukemia, osteosarcoma, leiomyoma, and rhabdomyoma, can be the targets. In particular, the vaccinia virus according to the present invention can be preferably used for treatment of lung cancer, pancreatic cancer, and ovarian cancer.

The pharmaceutical composition used for treatment of cancer comprising the mitogen-activated protein kinase-dependent vaccinia virus according to the present invention comprises, as an active ingredient, a pharmaceutically effective amount of the mitogen-activated protein kinase-dependent vaccinia virus according to the present invention. Such pharmaceutical composition may be in the form of a sterile aqueous or non-aqueous solution, a suspension, or an emulsion. In addition, the pharmaceutical composition may comprise a pharmaceutically acceptable diluent, auxiliary agent, carrier, or the like, such as salt, buffer, or adjuvant. Various routes of parenteral administration, such as a hypodermic, intravenous, intradermal, intramuscular, intraperitoneal, intranasal, or percutaneous route, may be employed. Alternatively, the pharmaceutical composition may be topically administered to a cancer lesion. The effective dose can be adequately determined on the basis of for example, age, sexuality, health conditions, and body weight of a subject. For example, the dose for a human adult is about $10^2$ to $10^{10}$ plaque-forming units (PFUs), and it is preferably $10^5$ to $10^6$ plaque-forming units (PFUs), although the dose is not limited thereto.

In addition, the mitogen-activated protein kinase-dependent vaccinia virus according to the present invention may comprise a foreign gene (i.e., foreign DNA or a foreign polynucleotide). Examples of foreign genes (i.e., foreign DNAs or foreign polynucleotides) include a marker gene, a therapeutic gene encoding a product having cytotoxic properties or immunostimulating effects, and DNAs encoding protein antigens of cancers, viruses, bacteria, and protozoa. A marker gene is also referred to as a reporter gene, and examples thereof include: fluorescent protein genes such as the luciferase (LUC) gene and the green fluorescent protein (GFP) gene; fluorescent protein genes such as the red fluorescent protein (DsRed); the β-glucuronidase (GUS) gene; the chloramphenicol acetyltransferase (CAT) gene; and β-galactosidase (LacZ) gene. The mitogen-activated protein kinase-dependent vaccinia virus comprising such a foreign gene can be referred to as a "mitogen-activated protein kinase-dependent vaccinia virus vector."

Therapeutic genes can be used for treatment of particular diseases, such as cancer or infectious diseases, and examples thereof include tumor suppressor genes, such as p53 and Rb, and genes encoding physiologically active substances, such as interleukin 1(IL-1), IL-2, IL-3, IL-4, IL-5, IL-6, IL-7, IL-8, IL-9, IL-10, IL-11, IL-12, IL-13, IL-14, IL-15, α-interferon, β-interferon, γ-interferon, angiostatin, thrombospondin, endostatin, METH-1, METH-2, GM-CSF, G-CSF, M-CSF, and tumor necrosis factors. Mitogen-activated protein kinase-dependent recombinant vaccinia viruses expressing luciferase or GFP enable simple and rapid detection of cancer cells that are infected with such viruses. When the mitogen-activated protein kinase-dependent vaccinia virus according to the present invention is used for treatment of cancer, oncolytic properties of the vaccinia virus and therapeutic genes against cancer can exert therapeutic effects on cancer.

As a foreign gene (foreign DNA), DNA encoding a virus, bacteria, protozoa, or cancer antigen may be introduced, so that a resulting vaccinia virus vector comprising a foreign gene introduced thereinto can be used as a vaccine against various viruses, bacteria, protozoa, or cancers. For example, genes encoding protective antigens (neutralizing antigens) of human immunodeficiency viruses, hepatitis viruses, herpes viruses, Mycobacteria, malaria parasites, severe acute respiratory syndrome (SARS) viruses, or cancer antigens may be introduced.

Such foreign genes can be introduced via, for example, homologous recombination. Homologous recombination may be implemented in accordance with the method described above. For example, a plasmid comprising a target foreign gene ligated to a site of interest in the DNA sequence may be prepared (i.e., a transfer vector), and the resulting plasmid may then be introduced into a cell infected with the vaccinia virus. A foreign gene is preferably introduced into a vaccinia virus through the site of a gene that is not essential for the life circle of the vaccinia virus.

When introducing a foreign gene, it is preferable that an adequate promoter be operably linked to a site upstream of the foreign gene. Examples of promoters that can be used include, but are not limited to PSFJ1-10, PSFJ2-16, p7.5K promoter, p11K promoter. T7.10 promoter, CPX promoter, HF promoter, H6 promoter, and T7 hybrid promoter. A foreign gene can be introduced into the vaccinia virus vector according to the present invention in accordance with a known technique for constructing a recombinant vaccinia virus vector. For example, a foreign gene can be introduced in accordance with the technique described in Experimental Medicine, extra issue, Protocol Series, Transgene & Expression Analysis Experiment Method, Saito et al. (ed.), YODOSHA (date of issue: Sep. 1, 1997) or DNA Cloning 4: Mammalian Systems (2nd edition), D. M. Glover et al (editors), Ikunoshin Kato (translation supervisor), TaKaRa, EMBO Journal (1987, Vol. 6, pp. 3379-3384).

The present invention is described in greater detail with reference to the examples below, although the technical scope of the present invention is not limited to such examples.

Example 1: Construction of Mitogen-Activated Protein Kinase (MAPK)-Dependent Recombinant Vaccinia Virus (MD-RVV)

Figure 2:
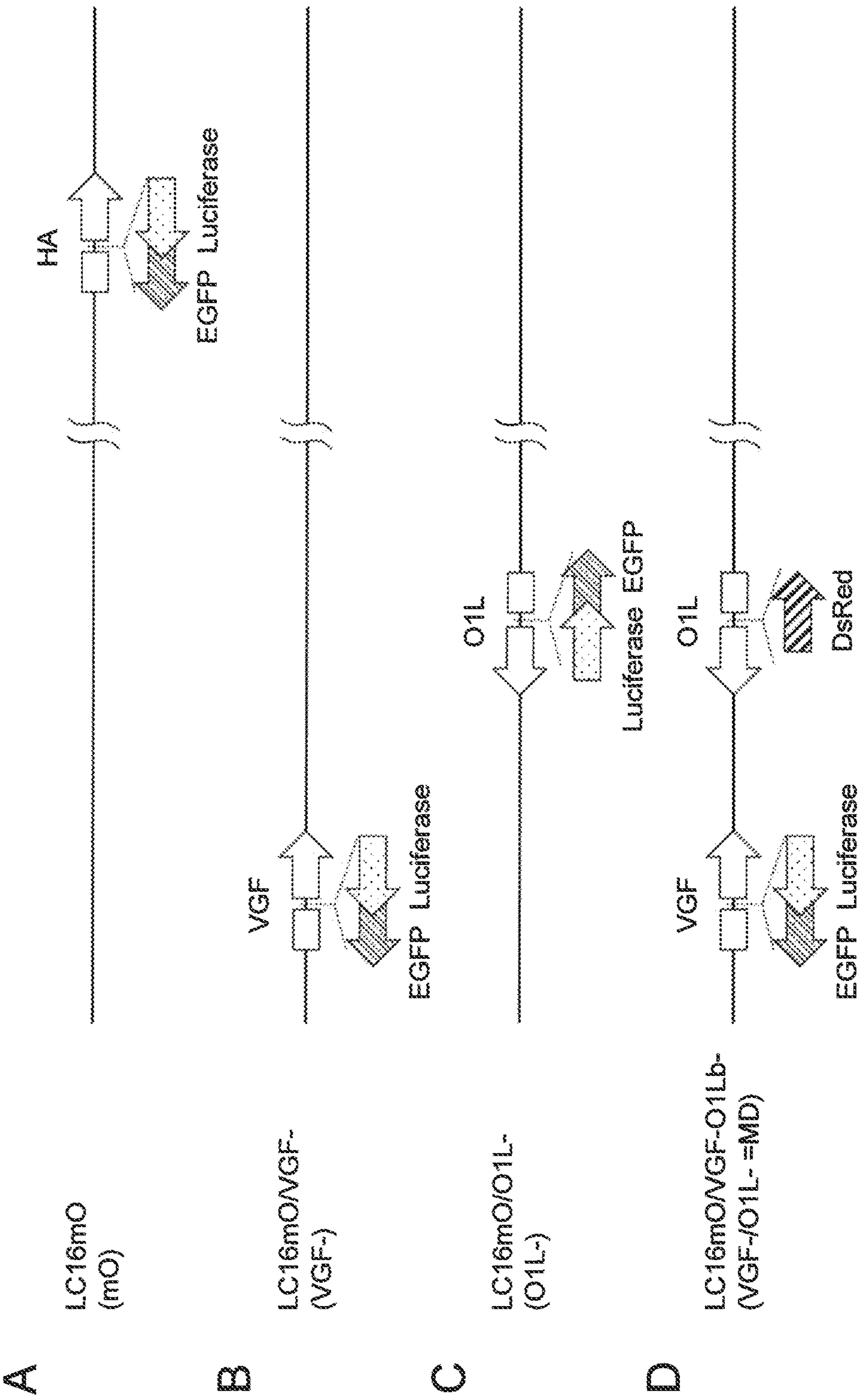
FIG. 2 shows the structures of the recombinant vaccinia viruses: LC16mO (mO); LC16mO/VGF− (VGF−); LC16mO/O1L− (O1L−); and LC16mO/VGF−O1L− (VGF−/O1L−).

In order to produce recombinant vaccinia virus strains lacking the functions of virus proteins VGF and O1L, a recombinant virus strain comprising a luciferase-GFP fusion gene expression cassette inserted into the VGF gene of the vaccine strain (LC16mO) (LC16mO/VGF− (VGF−)), a recombinant virus strain comprising a luciferase-GFP fusion gene expression cassette inserted into the O1L gene (LC16mO/O1L− (O1L−)), and a recombinant virus strain comprising a luciferase-GFP fusion gene expression cassette inserted into the VGF gene and a DsRed expression cassette inserted into the O1L gene (LC16mO/VGF−O1L− (VGF−/O1L−)) (MD) were produced. As a control virus strain, a recombinant virus strain comprising a luciferase-GFP fusion gene expression cassette inserted into the HA gene that would not affect the viral growth capacity of the LC16mO strain (mO) was used. FIG. 2 shows the structures of the resulting recombinant vaccinia virus strains. In FIGS. 2A, B, C, and D show the structure of LC16mO (mO), that of LC16mO/VGF− (VGF−), that of LC16mO/O1L− (O1L−), and that of LC16mO/VGF−O1L− (VGF−/O1L−), respectively.

With the use of genomic DNA of the LC16mO strain as a template, at the outset, the VGF gene region was amplified using two primers (5'-cgcggatcctattctcattcatattctct-3' (SEQ ID NO: 3) and 5'-cgcaagcttagatctggaaaatgtctgttagt-3' (SEQ ID NO: 4)), and the O1L gene region was amplified using two primers (5'-gcgctagcttaacgagttccatttatat-3' (SEQ ID NO: 5) and 5'-gcgctagcatgttcatgtatccggaattt-3' (SEQ ID NO: 6)). Each PCR product was cleaved with the restriction enzymes BamHI and HindIII or NheI, and the resultant was cloned into the same restriction enzyme site of the pUC19 vector to construct pUC19-VGF or pUC19-O1L.

With the use of genomic DNA of the LC16mO strain as a template, separately, the TK gene region was amplified using two primers (5'-cgcagctgagcttttgcgatcaataaatg-3' (SEQ ID NO: 7) and 5'-ttcagctgaatatgaaggagcaa-3' (SEQ ID NO: 8)). The PCR product was cleaved with the restriction enzyme PvuII, and the resultant was cloned into the same restriction enzyme site of the pUC19 vector to construct pTK. In addition, two synthetic DNAs (i.e., 5'-aattgcatgcgtcgacattaatggccggaccggccttcgaag-3' (SEQ ID NO: 9) and 5'-aattcttcgaaggccggtccggccattaatgtcgacgcatgc-3' (SEQ ID NO: 10)) were annealed to each other, and the resultant was cloned into pTK that had been cleaved with the restriction enzyme EcoRI to construct pTK-MSC. In order to insert a synthetic vaccinia virus promoter (Hammond J M. et al., Journal of Virological Methods, 1997, 66 (1): 135-138), two synthetic DNAs (i.e., 5'-tcgaaattggatcagcttttttttttttttttggcatataaataaggtcgaggtaccaaaaattgaaaaactattctaatttattgcacggccggac-3' (SEQ ID NO: 11) and 5'-cggccgtgcaataaattagaatagtttttcaatttttggtacctcgaccttatttatatgccaaaaaaaaaaaaaaaaaagctgatccaatt-3' (SEQ ID NO: 12)) were annealed to each other, and the resultant was cloned into pTK-MSC cleaved with the restriction enzymes SfiI and SalI to construct pTK-SP-MSC. The Luc/IRES/EGFP gene fragment was isolated from the pVNC110-Luc/IRES/EGFP plasmid using the restriction enzyme SfiI and EcoRI and cloned into the same restriction enzyme site of pTK-SP-MSC to construct pTK-SP-LG.

With the use of plasmid DNA of pGL4.20 (Promega KK.) as a template, a firefly luciferase gene region was amplified using two primers (5'-caacccgggccatggaagatgccaaaaaca-3' (SEQ ID NO: 13) and 5'-ctgcggccgccacggcgatcttgccgccct-3' (SEQ ID NO: 14)). The PCR product was cleaved with the restriction enzymes SmaI and NotI, and the resultant was cloned into the same restriction enzyme site of the pIRES vector (Clontech Laboratories, Inc.) to construct pIRES-Luc. With the use of plasmid DNA of pEGFP-N1 (Clontech Laboratories, Inc.) as a template, the EGFP gene region was amplified using two primers (5'-gcgcggccgcagccaccatggtgagcaagggcgagga-3' (SEQ ID NO: 15) and 5'-gctgcggccgctcgaattcttacttgtacagctcgtcca-3' (SEQ ID NO: 16)). The PCR product was cleaved with the restriction enzyme NotI, and the resultant was cloned into the same restriction enzyme site of the pIRES-Luc to construct pIRES-LucGFP. pIRES-LucGFP was cleaved with the restriction enzymes SmaI and EcoRI to obtain a LucGFP fragment, and the resulting LucGFP fragment was cloned into a vector fragment obtained by cleaving pTK-SP-LG with SfiI, blunt-ending the same, and then cleaving the blunt-ended fragment with EcoRI. Thus, pTK-SP-LucGFP was constructed.

pTK-SP-LucGFP was cleaved with the restriction enzymes SphI and EcoRI and blunt-ended, so as to obtain the SP-LucGFP fragment. Thereafter, the resulting SP-LucGFP fragment was cloned into a site at which pUC19-VGF was cleaved with the restriction enzyme AccI and blunt-ended, so as to construct pUC19-VGF-SP-LucGFP. Alternatively, the SP-LucGFP fragment was cloned into a site at which pUC19-O1L was cleaved with the restriction enzyme XbaI and blunt-ended, so as to construct pUC19-O1L-SP-LucGFP. Also, pTK-SP-LucGFP was cleaved with the restriction enzymes SphI and EcoRI and blunt-ended, so as to obtain the SP-LucGFP fragment. The resulting SP-LucGFP fragment was cloned into a site at which pVNC110 (Suzuki H. et al., Vaccine, 2009; 27 (7): 966-971) was cleaved with the restriction enzyme SpeI and blunt-ended, so as to construct pVNC110-SP-LucGFP.

Instead of the synthetic vaccinia virus promoter, separately, the p7.5K promoter was cloned into a site of pTK-MSC cleaved with the restriction enzymes SphI and SalI to construct pTK-P-MSC. The DsRed-Express gene region of pDsRed-Express-N1 (Clontech Laboratories, Inc.) was cloned into pCR4 (Invitrogen) to construct pCR4-DsRed. pCR4-DsRed was cleaved with the restriction enzymes PmeI and NotI and blunt-ended, so as to obtain the DsRed fragment. The resulting DsRed fragment was cloned into a site at which pTK-P-MSC was cleaved with SalI and blunt-ended, so as to construct pTK-P-DsRed. pTK-P-DsRed was cleaved with the restriction enzyme SphI and blunt-ended, so as to obtain the P-DsRed fragment. Thereafter, the resulting P-DsRed fragment was cloned into a site at which pUC19-O1L was cleaved with the restriction enzyme XbaI and blunt-ended, so as to construct pUC19-O1L-P-DsRed.

In order to collect mitogen-activated protein kinase-dependent recombinant vaccinia viruses having the virus genomes as shown FIG. 2, the RK13 cells that had been cultured to 80% confluence in a 6-well dish were infected with the vaccinia viruses (LC16mO) at an MOI of 0.02 to 0.1, and the viruses were allowed to adsorb to the cells at room temperature for 1 hour. Thereafter, FuGENE HD (Roche) was mixed with plasmid DNA of the transfer vector (pUC19-VGF-SP-LucGFP, pUC19O1L-SP-LucGFP, or pVNC110-SP-LucGFP), the resultant was incorporated into the cells in accordance with the instructions, and culture was conducted at 37° C. for 2 to 5 days. The cells were freeze-thawed, sonicated, adequately diluted, and inoculated into the RK13 cells that had almost reached confluence. Eagle MEM containing 0.8% methyl cellulose and 5% FBS medium were added, and culture was conducted at 37° C. for 2 to 5 days. The media were removed, large plaques were scraped with a chip end, and the plaques were suspended in Opti-MEM medium (Invitrogen). This procedure was repeated 3 or more times with the RK13 cells to purify the plaques. The plaque suspension sampled after plaque purification was sonicated, 200 μl of the suspension was centrifuged at 15,000 rpm for 30 minutes, and 50 μl of sterile distilled water or 10 mM Tris-HCl (pH 7.5) was added to the precipitate. After the suspension was sonicated for 30 seconds, the suspension was heated at 95° C. for 10 minutes to extract genomic DNA, and the extracted genomic DNA was subjected to screening via PCR. VGF was subjected to PCR with the use of two primers (5'-atgttgataaattatctga-3' (SEQ ID NO: 17) and 5'-ttatggcacaaccatatct-3' (SEQ ID NO: 18)), O1L was subjected to PCR with the use of two primers (5'-acagggattaagacggaaag-3' (SEQ ID NO: 19) and 5'-gtcaacaagcatcttccaac-3' (SEQ ID NO: 20)), and HA was subjected to PCR with the use of two primers (5'-cgactatagacataatacta-3' (SEQ ID NO: 21) and 5'-cagatgatgcacttactgta-3' (SEQ ID NO: 22)). Clones in which PCR products of given sizes had been detected were examined in terms of their nucleotide sequences via direct sequencing. Virus clones not presenting any problems in terms of nucleotide sequences were selected, mass-cultured in the RK13 cells, and then purified. Thereafter, the virus titer was measured in the RK13 cells and the viruses were then subjected to experimentation. In order to collect the VGF−/O1L-mitogen-activated protein kinase-dependent recombinant vaccinia viruses, the RK13 cells that had been cultured in the manner described above were infected with VGF− viruses at an MOI of 0.02 to 0.1, and the viruses were allowed to adsorb to the cells at room temperature for 1 hour. Thereafter, FuGENE HD (Roche) was mixed with plasmid DNA of the transfer vector (pUC19-O1L-P-DsRed), the resultant was incorporated into the cells in accordance with the instructions, and culture was conducted at 37° C. for 2 to 5 days. The viruses were collected in the manner described above and subjected to experimentation as the VGF−/O1L− virus strains.

Figure 3:
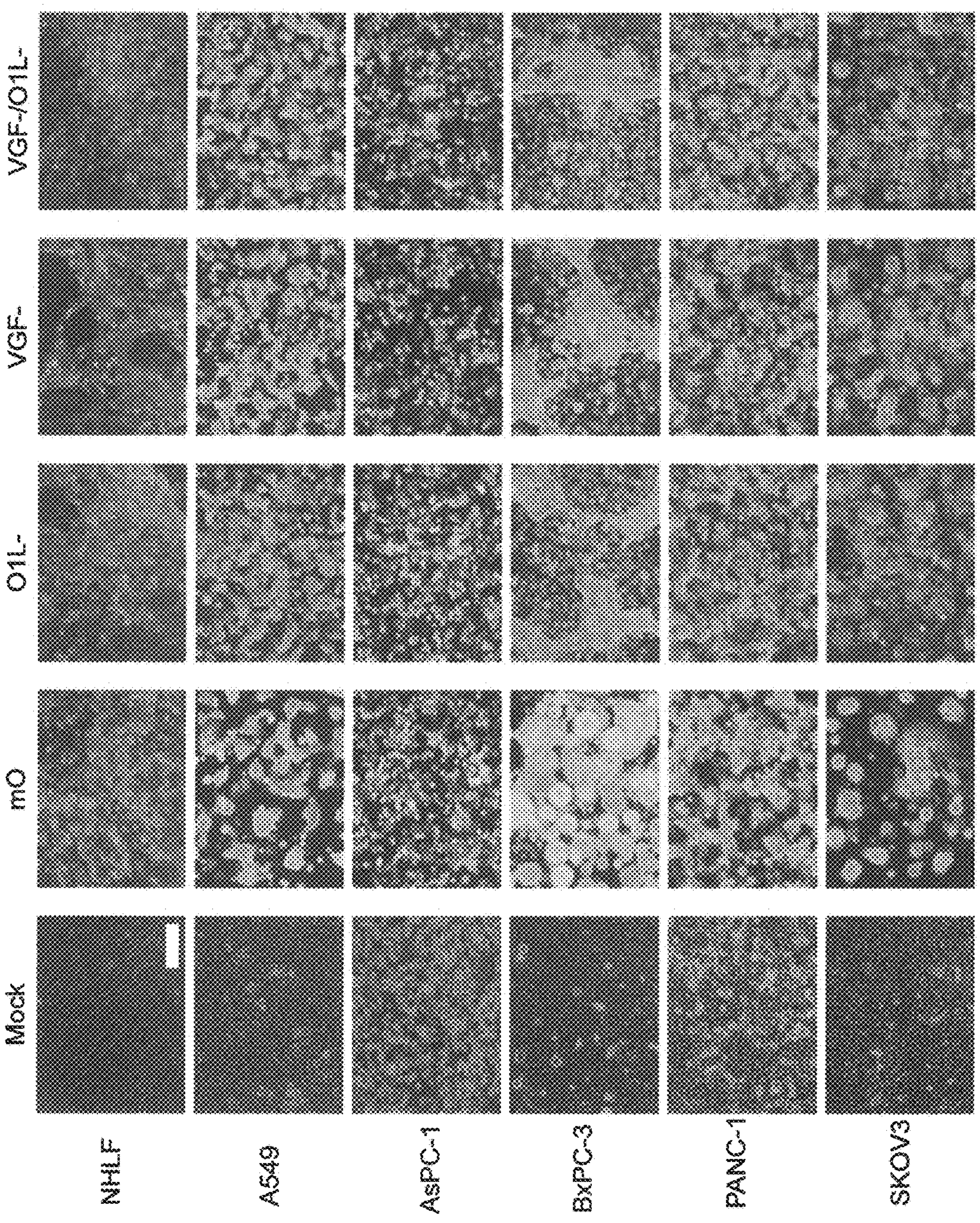
FIG. 3 shows cytotoxicity of MD-RVV on normal cells and tumor cells in the presence of serum.
Figure 4:
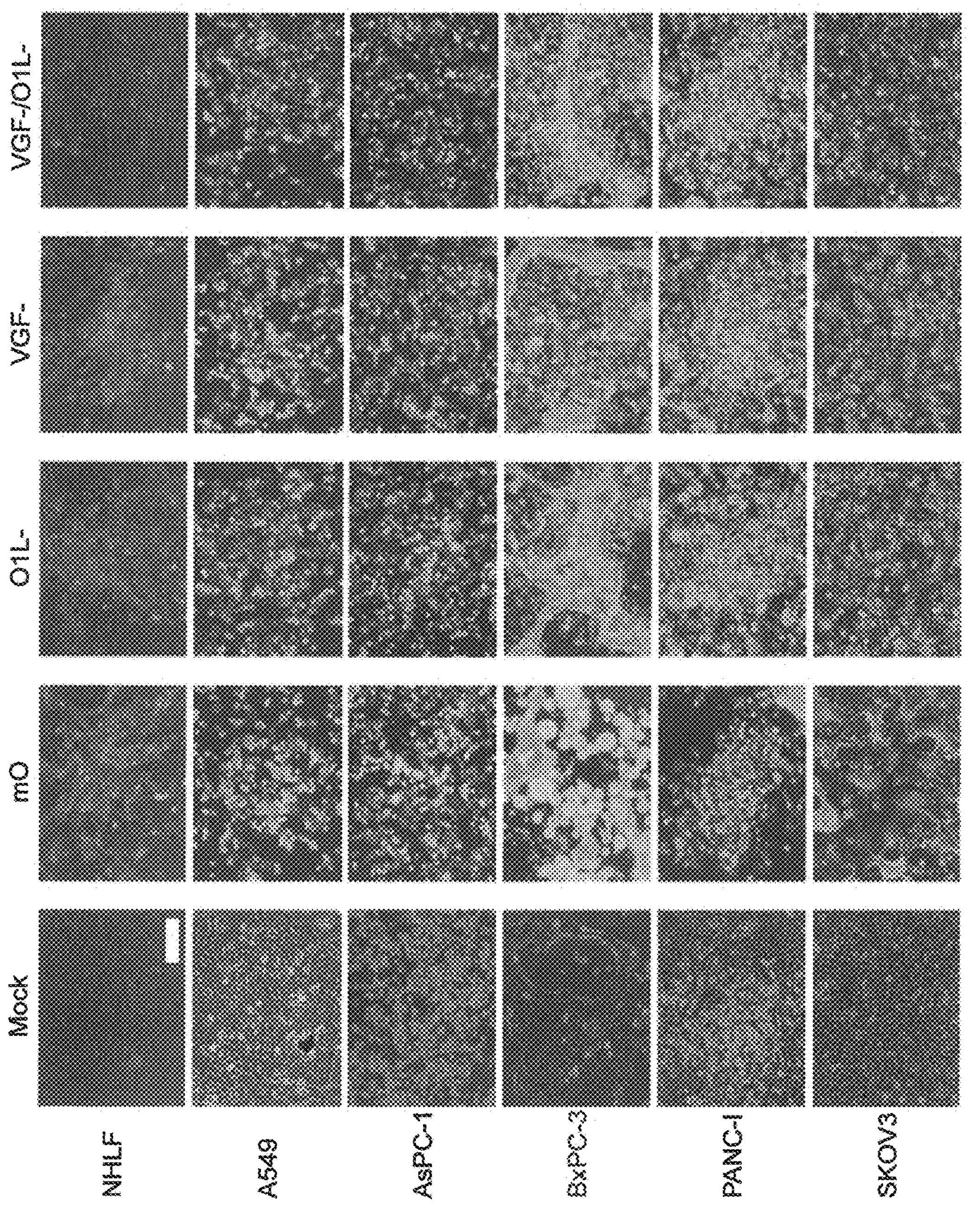
FIG. 4 shows cytotoxicity of MD-RVV on normal cells and tumor cells in the absence of serum.

Example 2: Properties of Mitogen-Activated Protein Kinase-Dependent Recombinant Vaccinia Virus Normal human lung fibroblasts (NHLF) and human cancer cell lines (lung cancer A549 cells, pancreatic cancer AsPC-1 cells, pancreatic cancer BxPC-3 cells, pancreatic cancer PANC-1 cells, and ovarian cancer SKOV3 cells) cultured in a 24-well dish in the presence or absence of serum were infected with mitogen-activated protein kinase-dependent recombinant vaccinia viruses having the virus genomes as shown in FIG. 2 at an MOI of 1, and culture was conducted at 37° C. for 30 hours. Thereafter, the live cells were observed under a fluorescent microscope (Olympus Corporation) by means of bright field imaging and fluorescence imaging, and the images were superposed on top of each other. As a result, the cytotoxicity of the viruses in normal cells was found to be substantially equivalent to that in cancer cells in the presence of serum, and the GFP protein expression levels were also substantially equivalent to each other (FIG. 3: the scale bar indicate 500 μm). FIG. 3 shows the results of infection of normal human lung fibroblasts (NHLF) and human cancer cell lines (lung cancer A549 cells, pancreatic cancer AsPC-1 cells, pancreatic cancer BxPC-3 cells, pancreatic cancer PANC-1 cells, and ovarian cancer SKOV3 cells) with the Mock (a control), the mO strain (mO), the VGF-deficient mO strain (VGF−), the O1L-deficient mO strain (O1L−), and the VGF−/O1L-deficient mO strain (VGF−/O1L−). The left part of each image shows the name of cells and the upper part shows the vaccinia viruses that had infected the cells. A green region in the figure indicates a fluorescence-stained site, which looks white in a monochrome image. In the absence of serum, however, GFP expression levels and cytotoxicity of various types of viruses were substantially equivalent to each other in cancer cells. The mO strain (mO) exhibited the highest GFP expression levels and the highest level of cytotoxicity in normal cells, followed by the VGF-deficient mO strain (VGF−) and the O1L-deficient mO strain (O1L−). GFP expression levels and cytotoxicity of the VGF−/O1L− strain were significantly lower than those of other viruses and substantially equivalent to those of a mock control cells (Mock) (FIG. 4: the scale bar indicates 500 μm). The images shown in FIG. 4 are the same as those shown in FIG. 3.

Figures 1, 5:
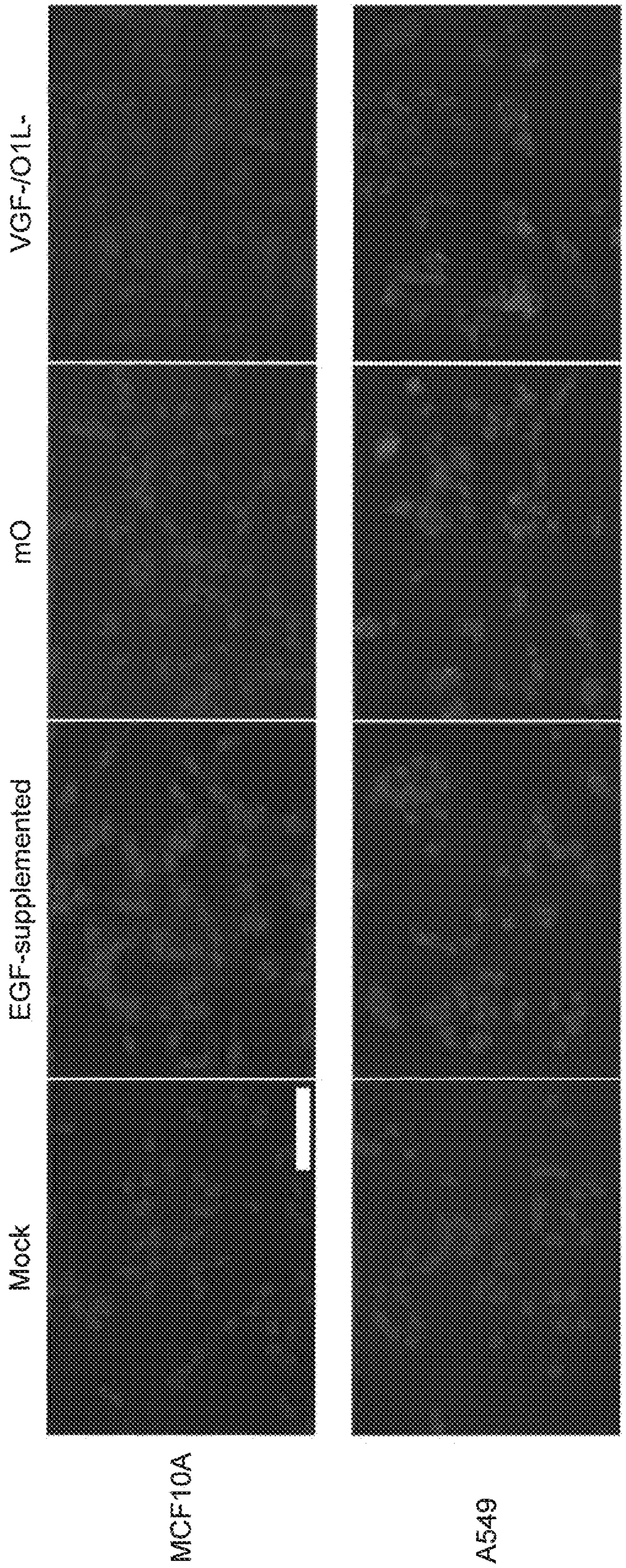
Figures 2, 5:
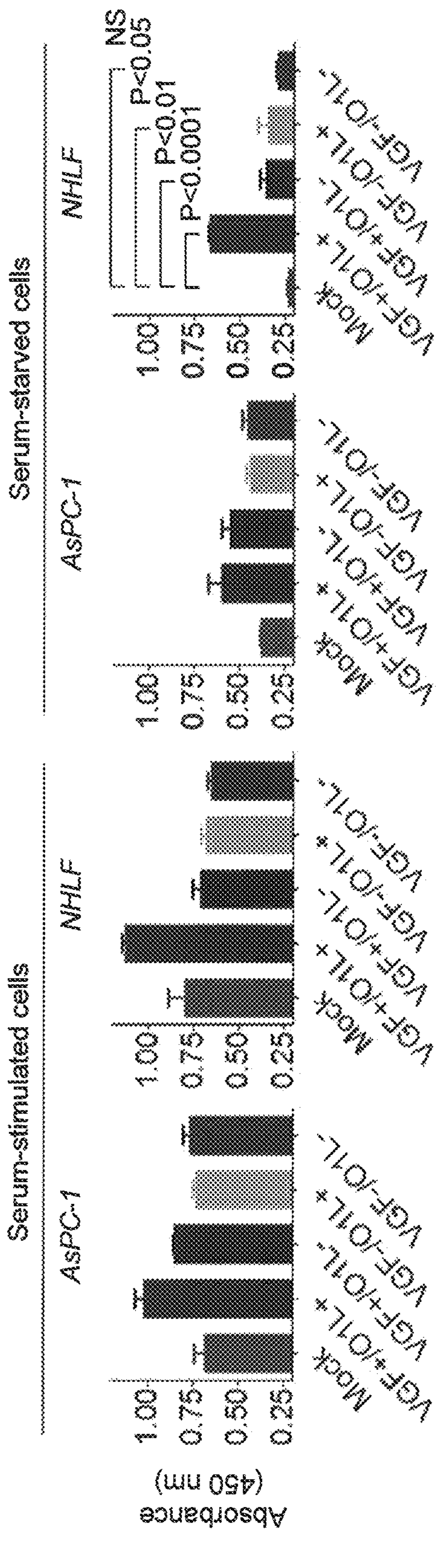

Subsequently, normal human mammary gland epithelial cells (MCF10A cells) and lung cancer A549 cells that had been cultured in the absence of serum on 8-well-chambered glass slides were infected with the mitogen-activated protein kinase-dependent recombinant vaccinia virus strains having the virus genomes as shown in FIG. 2 (i.e., the mO or VGF−/O1L− strains) at an MOI of 1. After culture had been conducted at 37° C. for 12 hours, the cells were fixed with 4% formaldehyde and subjected to methanol permeabilization. (While the GFP protein was observed after the treatment, the DsRed protein was not observed.) The cells were incubated with the primary antibody (#4370, CST Japan) that would detect the phosphorylated p44/42 MAPK protein (Erk1/2). After the cells were washed with PBS, the washed cells were stained with the secondary fluorescent (Alexa Fluor 568) antibody (#A21069, Invitrogen). The resultants were observed under a fluorescence microscope (Olympus Corporation) with the addition of a mounting medium containing a nuclear stain, DAPI, and the stained images were synthesized. As positive controls, the epidermal growth factors (EGF proteins) were added at a density of 200 ng/ml 15 minutes before fixation. FIG. 5-1 shows the results of infection of normal human mammary gland epithelial cells (MCF10A cells) or lung cancer A549 cells (indicated on the left side of each image) with the Mock (a control), the EGF-stimulation (a positive control), the mO strain (mO), or the VGF−/O1L-deficient mO strain (VGF−/O1L−) (with the scale bar indicating 500 μm). While the nuclei were selectively stained blue in the mock MCF10A cells, the phosphorylated p44/42 MAPK proteins were stained red in the nuclei and the cytoplasm of the mock A549 cells. In both EGF-stimulated MCF10A cells and A549 cells, the cell nuclei were stained blue and the phosphorylated p44/42 MAPK proteins were stained intense red in the cytoplasm. In the MCF10A cells and the A549 cells infected with mO, expression of the mO virus-derived GFP proteins was observed, the cell nuclei were stained blue in the infected cells and uninfected cells in the vicinity thereof, and the phosphorylated p44/42 MAPK proteins were stained intense red in the cytoplasm. In the cells infected with VGF−/O1L−, the nuclei were stained blue but the phosphorylated p44/42 MAPK proteins were not stained in the MCF10A cells. That is, the number of cells expressing the VGF−/O1L-virus-derived GFP proteins was lower than the number of cells expressing the mO-virus-derived GFP proteins. In the A549 cells, in contrast, the phosphorylated p44/42 MAPK proteins were stained red as with the Mock, and the number of cells expressing the VGF−/O1L-virus-derived GFP proteins was equivalent to the number of cells expressing the mO-virus-derived GFP proteins.

The normal human lung fibroblasts (NHLF) and human pancreatic cancer cells (AsPC-1) that had been cultured in a 96-well plate in the presence or absence of serum were infected with the mitogen-activated protein kinase-dependent recombinant vaccinia virus strains having the virus genomes as shown in FIG. 2 (mO, VGF−, O1L−, or VGF−/O1L−) at an MOI of 1, and culture was conducted at 37° C. for 30 hours. Thereafter, endogenous phosphorylated 44/42 MAPK protein (Erk1/2) levels were detected using the Pierce ERK1/2 Colorimetric In-Cell ELISA Kit (62206. Thermo Scientific). The results are shown in FIG. 2 shows the results when normal NHLF cells or pancreatic cancer AsPC-1 cells cultured in the presence of serum (i.e., serum-stimulated cells) or in the absence of serum (i.e., serum-starved cells) were infected with the Mock (the control), the mO strain (VGF+/O1L+), the O1L-deficient mO strain (VGF+/O1L−), the VGF-deficient mO strain (VGF−/O1L+), or the VGF−/O1L-deficient mO strain (VGF−/O1L−) (and the absorbance at 450 nm on the vertical axis indicates the phosphorylated Erk1/2 level). In the normal NHLF cells and the pancreatic cancer AsPC-1 cells cultured in the presence of serum, a high degree of ERK activation was observed, regardless of virus type or infection therewith. In pancreatic cancer AsPC-1 cells cultured in the absence of serum, in contrast, the phosphorylated Erk1/2 level is reduced to almost half of the original level, and an equivalent degree of ERK activation is observed, regardless of virus type or infection therewith. In normal NHLF cells that had been cultured in the absence of serum, however, the phosphorylated Erk1/2 level was drastically reduced in the cells infected with VGF−/O1L−, and there were no significant differences in terms of the phosphorylated Erk1/2 levels between the cells infected with VGF−/O1L− and the control virus-uninfected cells. Meanwhile, the phosphorylated Erk1/2 levels cells infected with VGF+/O1L+, VGF+/O1L−, or VGF−/O1L+ were significantly enhanced compared with the phosphorylated Erk1/2 levels in control cells. As described above, the growth capacity of the mitogen-activated protein kinase-dependent recombinant vaccinia virus strain (VGF−/O1L−) is reduced significantly in normal cells in which the Ras/Raf/MEK/ERK metabolic pathway is not activated. In cancer cells in which the Ras/Raf/MEK/ERK metabolic pathway is activated, the functions of the VGF−/O1L− viruses for activating ERK are complemented, and viruses can thus grow.

Figure 6A:
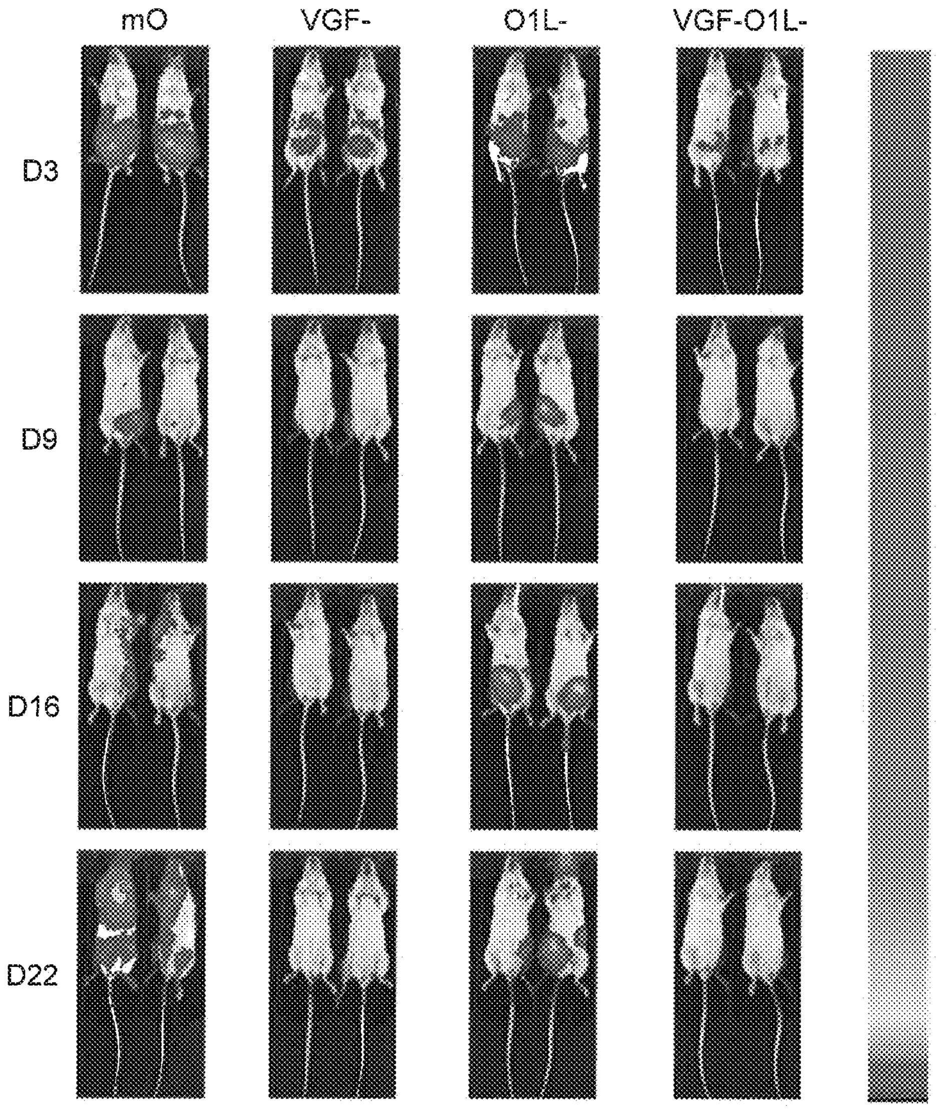
FIG. 6A shows virus distribution in vivo after the viruses have been inoculated into the immunodeficient SCID mouse.
Figure 6B:
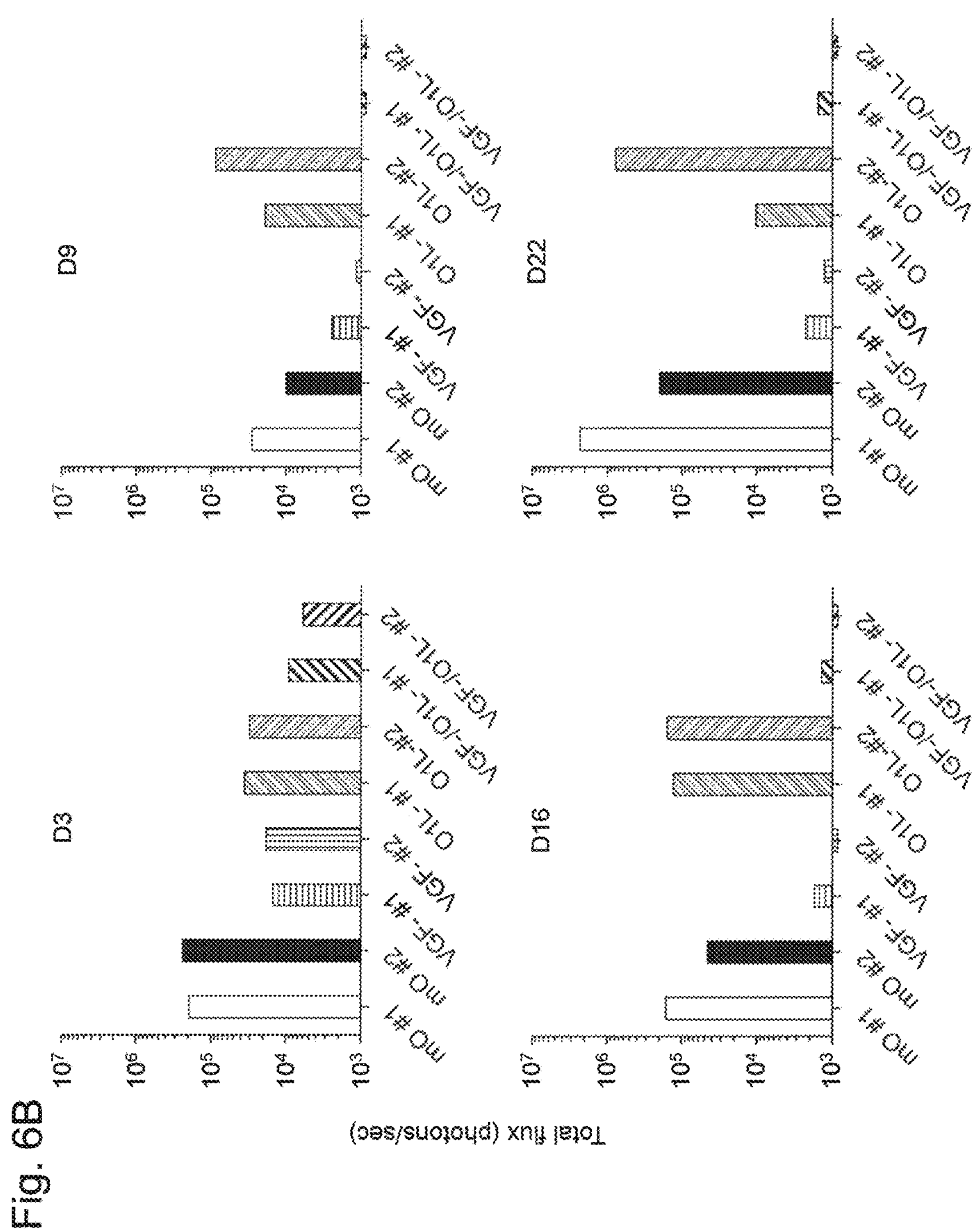
FIG. 6B shows the results of quantification of viruses grown after the viruses have been inoculated into the immunodeficient SCID mouse.

Example 3: Safety of Mitogen-Activated Protein Kinase-Dependent Recombinant Vaccinia Virus The viral pathogenicity of the mitogen-activated protein kinase-dependent recombinant vaccinia virus strains in the mouse body was examined. Since ERK cannot be activated in normal cells that have been infected with the mitogen-activated protein kinase-dependent recombinant vaccinia virus strain (VGF−/O1L−), mitosis is not promoted. As a result, the reduction in viral growth is presumed to be significant. The mitogen-activated protein kinase-dependent recombinant vaccinia virus strains having the virus genomes as shown in FIG. 2 ($10^6$ pfu) were administered intraperitoneally to SCID mice (each group consisting of two mice). Luciferin was administered 3 days (D3), 9 days (D9), 16 days (D16), and 22 days (D22) after the administration luciferase expression in virus-infected cells in which viruses grew (i.e., the number of grown viruses) was subjected to non-invasive observation using an in vivo imaging system (Berthold, NightDHADE LB985) (FIG. 6A), and the results of observation were quantified (FIG. 6B). As a result, the highest luciferase expression level was observed in the mice to which mO− had been administered 3 days after virus administration, followed by the mice to which O1L− had been administered, the mice to which VGF− had been administered, and the mice to which VGF−/O1L− had been administered; however, the luciferase expression was not observed in mice to which VGF−/O1L− had been administered 9 days after virus administration. Thereafter, viral infection and viral growth were observed in the mice to which mO had been administered and the mice to which O1L− had been administered, viral infection and viral growth spread throughout the body, in addition to within the abdominal cavity in which the viruses had been administered, with the elapse of time, and the area of infection was consistent with papules developed primarily in tails, limbs, and oral cavities. In contrast, viruses disappeared from the mice to which VGF− had been administered and the mice to which VGF−/O1L− had been administered. Virus types (i.e., mO strains (mO), VGF-deficient mO strains (VGF−), O1L-deficient mO strains (O1L−), and VGF−/O1L-deficient in mO strains (VGF−/O1L−)) are indicated on top of the images in FIG. 6A and below the charts in FIG. 6B. The number of days after administration is indicated on the left side of the images in FIG. 6A and on top of the charts in FIG. 6B. In FIG. 6A, the bar shown on the right side of images indicates the luminous intensity of a light source induced by luciferase (i.e., the power of light) in the order of red, orange, yellow, greenish yellow, blue, and purple from the top to the bottom. In FIG. 6B, the total number of photons/sec, which is the unit indicating the light intensity, is indicated on the vertical axis.

Figure 7:
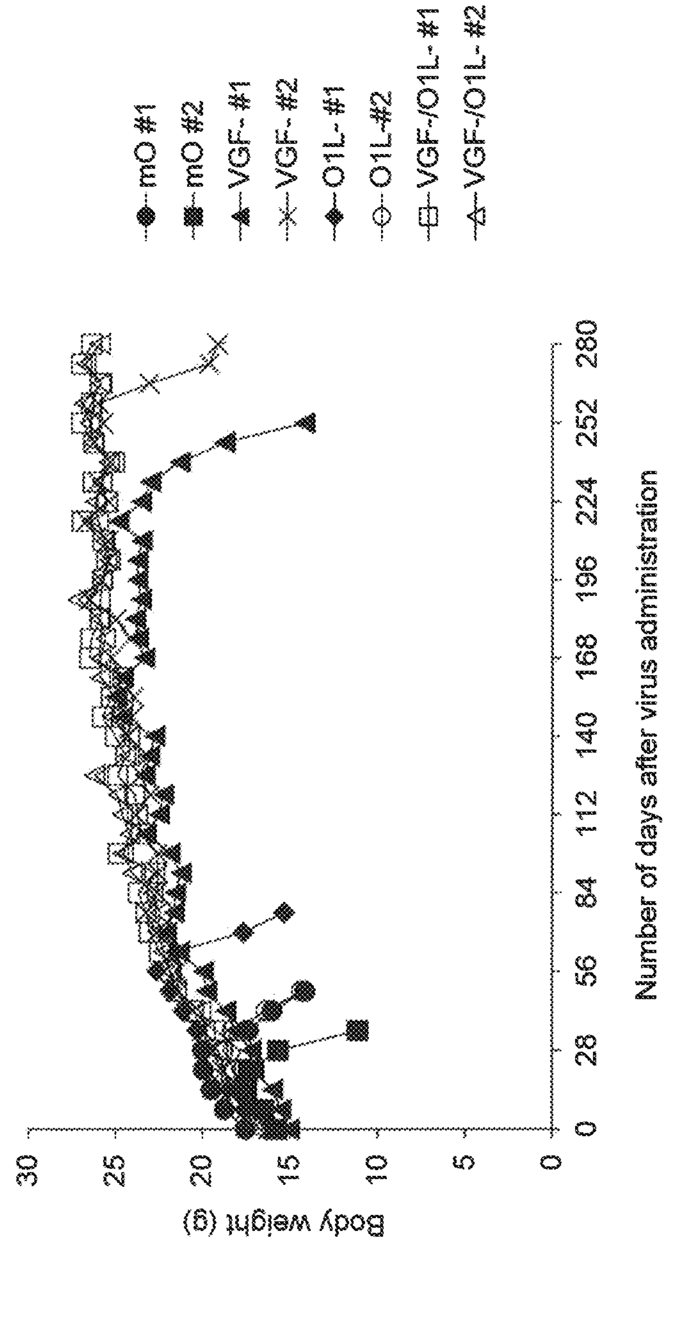
FIG. 7 shows changes in the body weight after the viruses have been inoculated into the immunodeficient SCID mouse.
Figure 8:
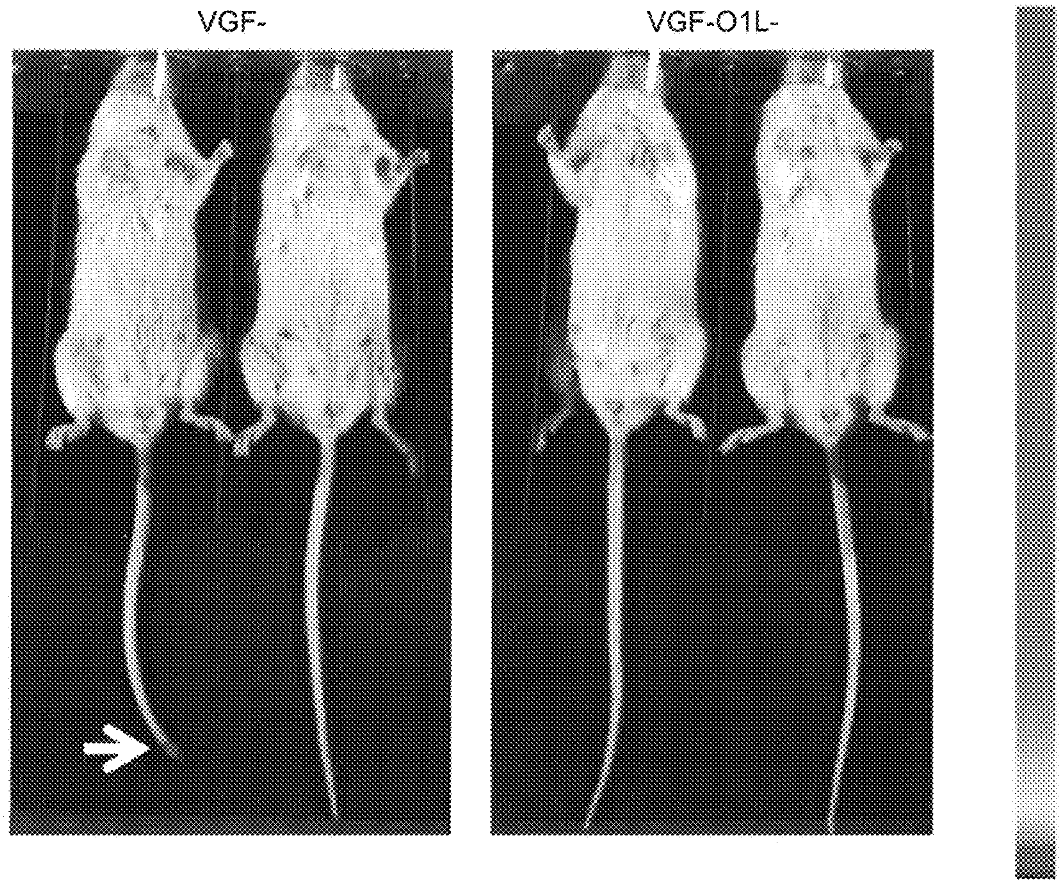
FIG. 8 shows the virus distribution in vivo 33 weeks after the viruses were inoculated into the immunodeficient SCID mouse.

Subsequently, changes in body weights of the mice to which viruses had been administered were observed for a long period of time (FIG. 7). Body weight loss was not observed in the mice to which VGF−/O1L− had been administered. That is, the viruses disappeared from the body. In contrast, the mice to which mO had been administered died 35 days and 49 days after administration because of virus virulence that would cause rapid weight loss. Also, the mice to which O1L− had been administered died 49 days and 77 days after administration. In some of the group of mice to which VGF− had been administered, in contrast, papular development was observed in tails approximately 217 days after administration, necrosis was also observed at the sites where papular development was observed, and rapid weight loss was observed. As a result of non-invasive imaging of luciferase expression 231 days after administration, the viral growth was observed at the sites where papular development was observed (→) (FIG. 8). Measurement conditions were the same as those shown in FIG. 6A, and the scale indicating the light intensity indicates the same range of light intensity in the order of red, orange, yellow, greenish yellow, blue, and purple from the top to the bottom. The mice to which VGF− had been administered died 252 days and 287 days after administration (FIG. 7). As described above, the mitogen-activated protein kinase-dependent recombinant vaccinia virus strains (VGF−/O1L−) lack the genes encoding the virus proteins for activating the Ras/Raf/MEK/ERK metabolic pathway (i.e., VGF and O1L). Accordingly, it was verified in the mouse body that the growth capacity of such vaccinia virus would significantly deteriorate in normal cells.

Figure 9:
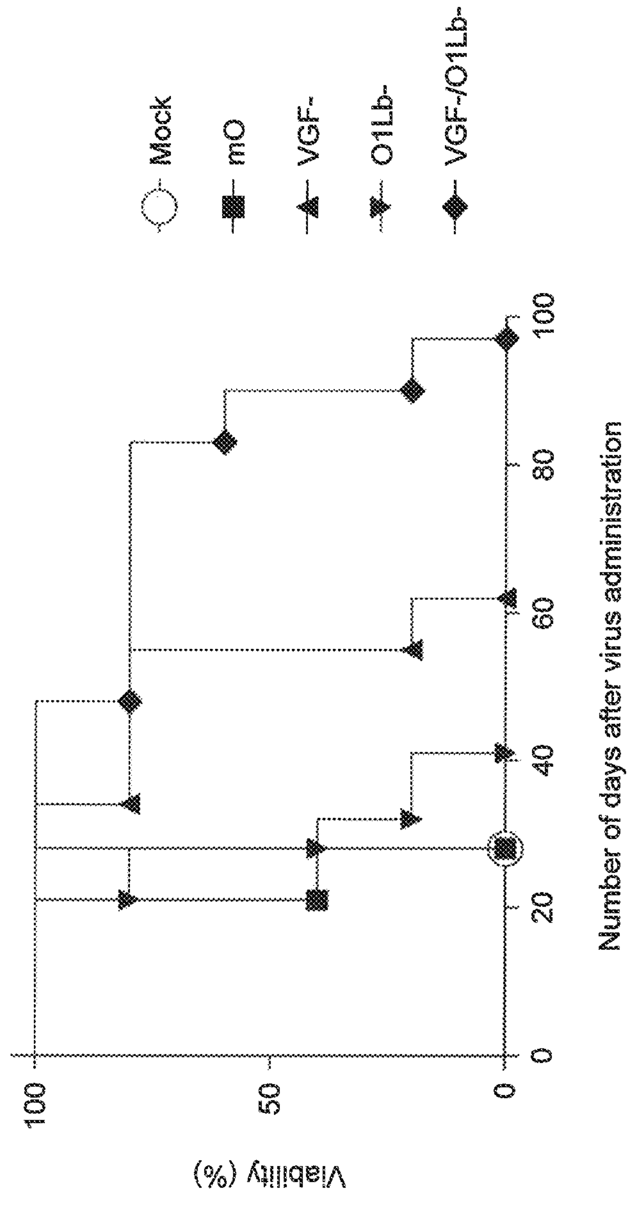
FIG. 9 shows the anti-cancer effects of the mitogen-activated protein kinase-dependent recombinant vaccinia virus on a mouse model for peritoneal dissemination of the human pancreatic cancer BxPC3.

Example 4: Anti-Cancer Effect of Mitogen-Activated Protein Kinase-Dependent Recombinant Vaccinia Virus Human pancreatic cancer BxPC-3 cells ($5\times10^6$ cells) stably expressing *Renilla* luciferase were administered intraperitoneally to SCID mice, and mitogen-activated protein kinase-dependent recombinant vaccinia virus strains ($10^6$ pfu each) were administered intraperitoneally 7 days thereafter (with each group consisting of 5 mice). As a result, VGF− or VGF−/O1L− was found to exert potent anti-cancer effects on mouse models for peritoneal dissemination of BxPC-3, the viability attained by virus administration was found to be significantly different from that observed in the mock control group to which no viruses had been administered as a result of the log-rank test (P=0.0047), and side effects resulting from virus virulence were not observed (FIG. 9). In addition, the viability attained by VGF−/O1L− was found to be significantly different from that attained by VGF− as a result of the log-rank test (P=0.031).

Figure 10A:
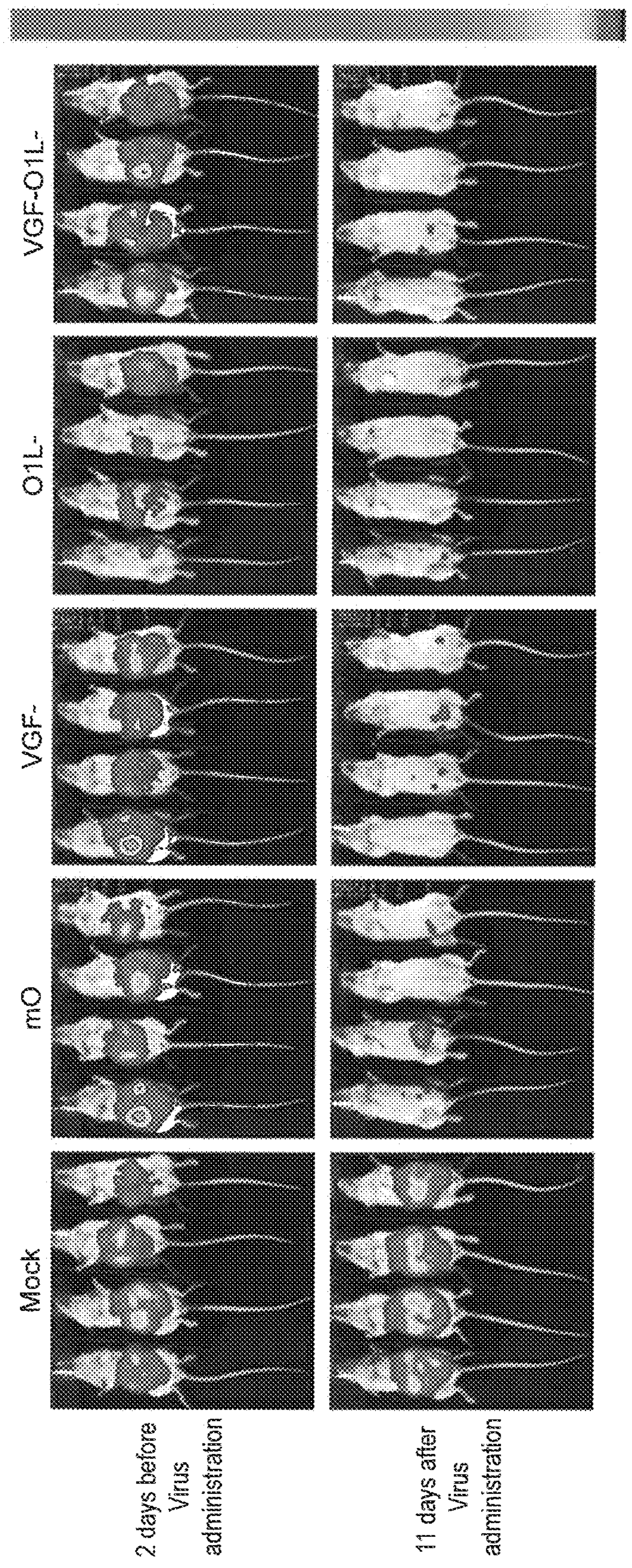
FIG. 10A shows the tumor distribution in vivo after the viruses have been inoculated into the mouse model for peritoneal dissemination of BxPC3.
Figure 10B:
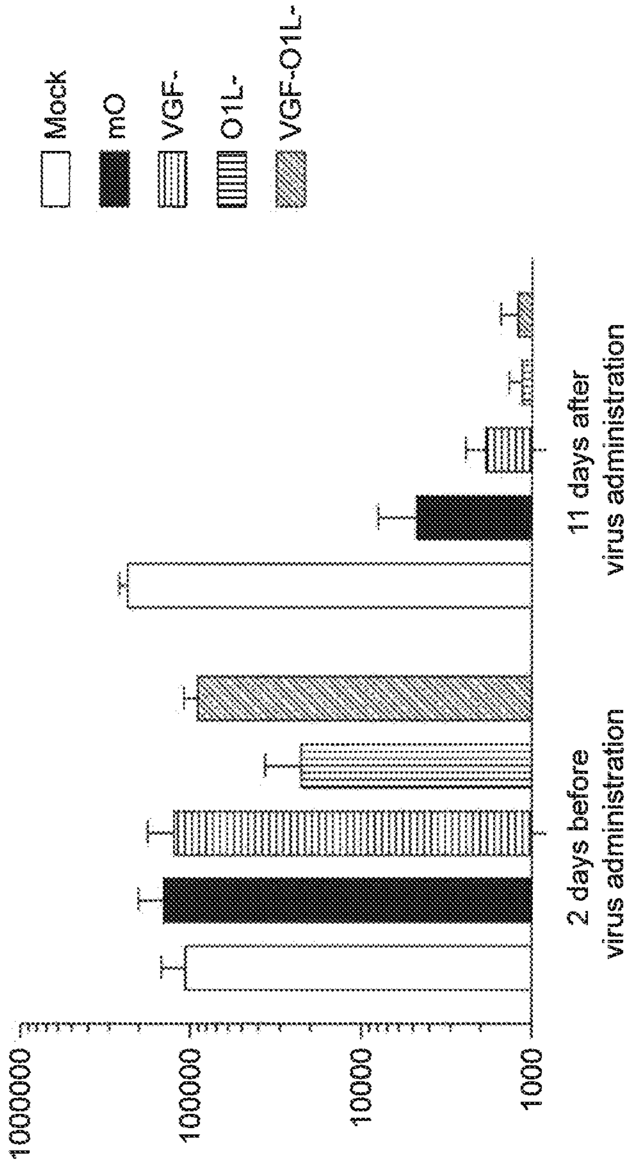
FIG. 10B shows the results of quantification of the tumor growth after the viruses have been inoculated into the mouse model for peritoneal dissemination of BxPC3.

Subsequently, coelenterazine, which is a *Renilla* luciferase substrate, was administered intraperitoneally 2 days before virus administration and 11 days after virus administration. The tumor cells (i.e., the number of grown cells) in the mouse body were subjected to non-invasive observation using an in viva imaging system (Berthold, NightDHADE LB985) (FIG. 10A), and the results of observation were quantified (FIG. 10B). As a result, peritoneal dissemination of BxPC-3 cells was observed 2 days before virus administration, and the tumors substantially disappeared from the abdominal cavity 11 days after the initiation of treatment in all groups to which viruses had been administered. In the control group, in contrast, no therapeutic effects were observed, and the growth of tumors was observed. In the case of mice to which VGF−/O1L− had been administered, the highest degree of improvement in viability was observed, and 97.4% to 99.3% of the tumor cells that had existed before treatment had disappeared 11 days after the initiation of treatment. Virus types (i.e., mO strains (mO), VGF-deficient mO strains (VGF−), O1L-deficient mO strains (O1L−), and VGF−/O1L-deficient mO strains (VGF−/O1L−)) are indicated on top of the images in FIG. 10A and on the right side of the bar graph in boxes in FIG. 10B. In FIG. 10, the bar shown on the right side of images indicates the luminous intensity of a light source induced by luciferase (i.e., the power of light) in the order of red, orange, yellow, greenish yellow, blue, and purple from the top to the bottom. In FIG. 10B, the total number of photons/sec, which is the unit indicating the light intensity, is indicated on the vertical axis.

Figure 11:
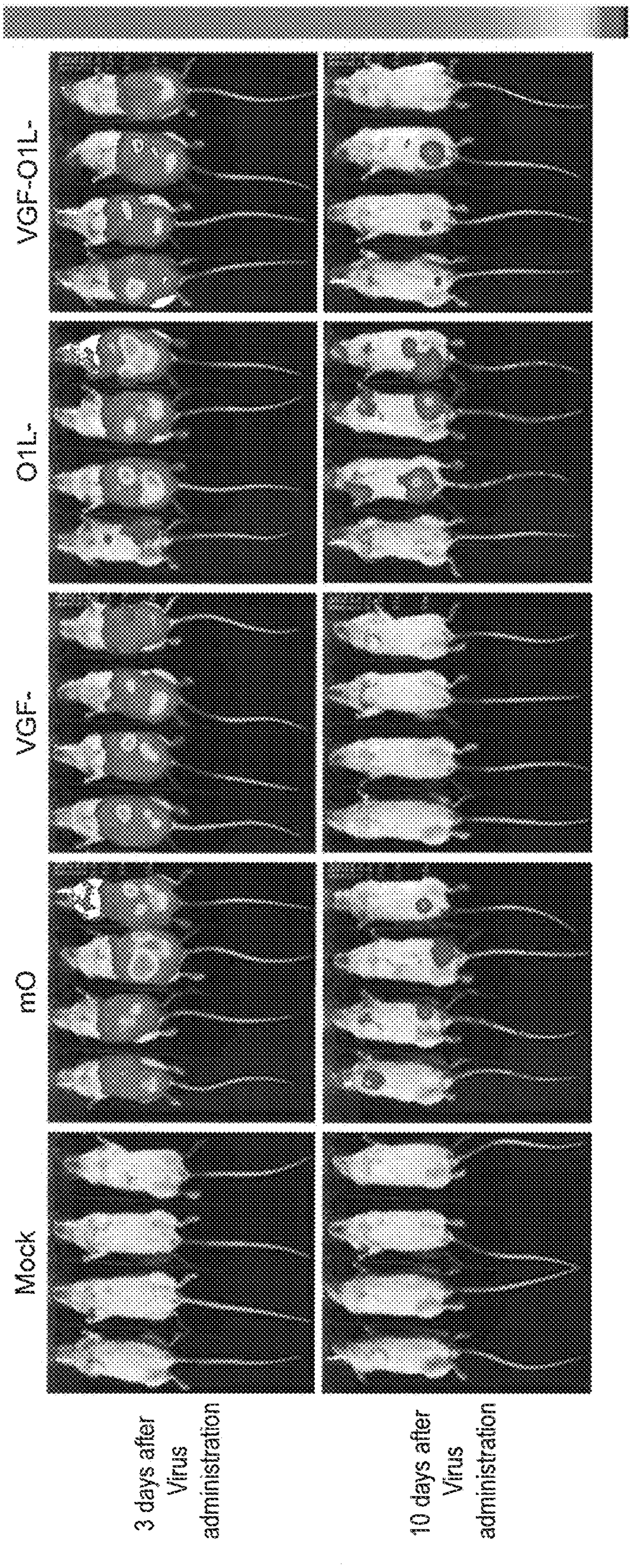
FIG. 11 shows the virus distribution in vivo after the viruses have been inoculated into the mouse model for peritoneal dissemination of BxPC3.

Subsequently, luciferin, which is a firefly luciferase substrate, was administered intraperitoneally 3 days and 10 days after virus administration, and the virus distribution in the mouse body was observed in a non-invasive manner. As a result, the growth of virus strains (mO, VGF−, O1L−, and VGF−/O1L−) was observed at equivalent levels in tumors in the abdominal cavity 3 days after administration. In addition to tumor tissues, the growth of viruses was observed in normal tissue of mice to which mO and O1L− had been administered 10 days after administration. When VGF− and VGF−/O1L− viruses were administered, however, viruses disappeared from the mouse body, or the growth of viruses was restricted to tumors in the abdominal cavity; that is, the growth of viruses was not observed in normal tissues (FIG. 11). Virus types (i.e., mO strains (mO), VGF-deficient mO strains (VGF−, O1L-deficient mO strains (O1L−), and VGF−/O1L-deficient mO strains (VGF−/O1L−)) are indicated on top of the images in FIG. 11.

Figure 12:
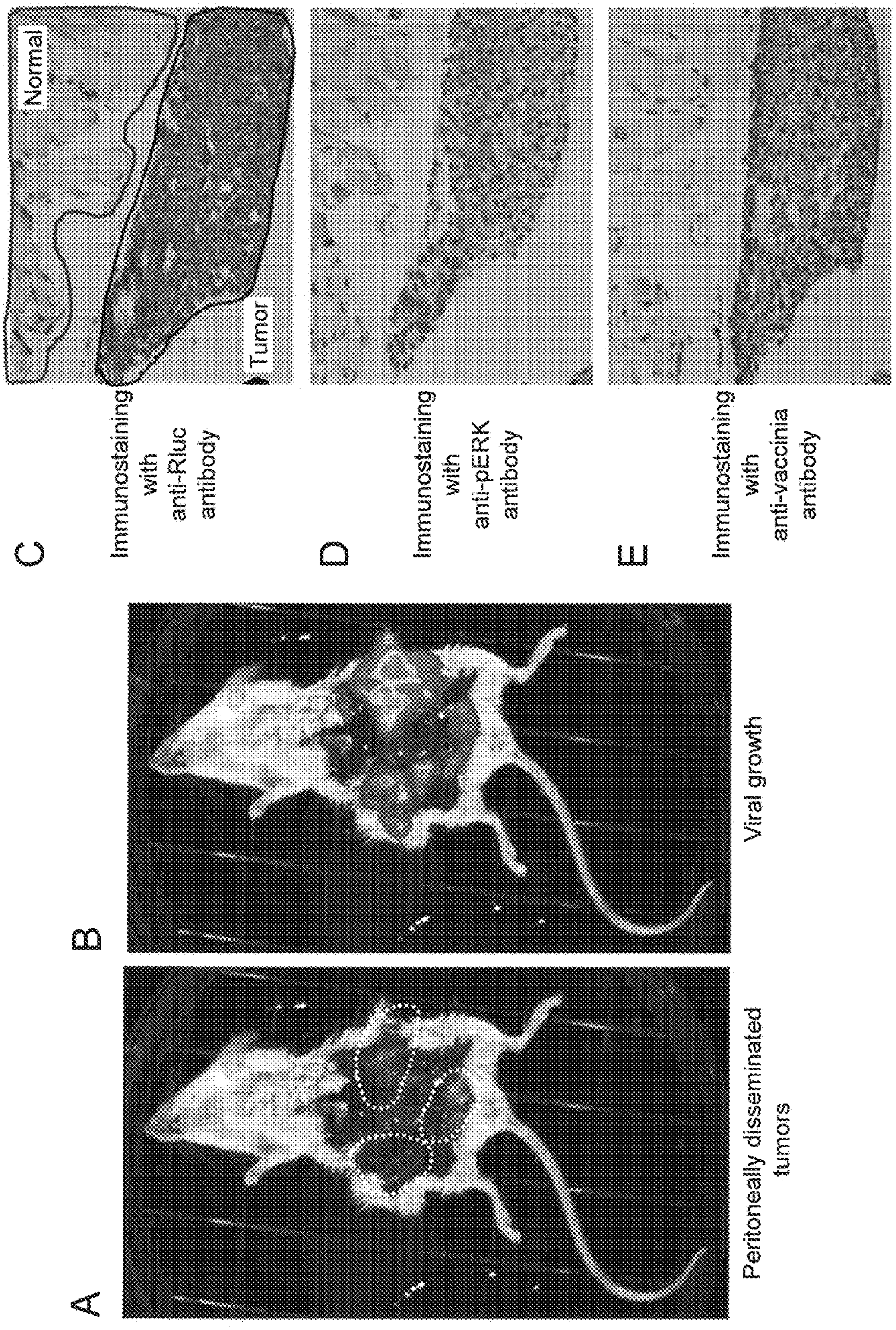
FIG. 12 shows the tumor-specific viral growth and the ERK activity in the mouse model for peritoneal dissemination of BxPC3.

In addition, luciferin, which is a firefly luciferase substrate, was administered intraperitoneally to similar mouse models for peritoneal dissemination of BxPC-3 3 days after administration of VGF−/O1L−, the mice were euthanized, and the inside of the abdominal cavity was directly observed (FIG. 12). As a result, peritoneal dissemination of tumor tissues (indicated by a dotted line in FIG. 12A) was detected (FIG. 12A), and luminescence indicating viral growth was also observed (FIG. 12B). Subsequently, tumor tissues including normal tissues were collected, the collected tissues were fixed with 10% formalin, and paraffin sections were then prepared. After deparaffinization, antigen activation treatment was carried out by the microwave method involving the use of 10 mM sodium citrate buffer (pH 6.0), and serial sections were blocked with a blocking solution (TBST/5% normal goat serum) at room temperature for 1 hour. The primary antibody (PM047, MBL) that would detect *Renilla* luciferase, the primary antibody (#4370, CST Japan) that would detect the phosphorylated p44/42 MAPK protein (Erk1/2), or the primary antibody (ab35219, abcam) that would detect the vaccinia virus was added to the sections and the resultants were incubated at 4° C. overnight, followed by washing. Thereafter, color was developed using the SignalStain® Boost IHC Detection Reagent (#8114, CST Japan) and the SignalStain® DAB Substrate Kit (#8059, CST Japan), and the sections were subjected to contrast staining with the use of hematoxylin. FIG. 12C shows the results of detection of *Renilla luciferase* (Rluc), FIG. 12D shows the results of detection of the phosphorylated p44/42 MAPK protein (Erk1/2) (pERK), and FIG. 12E shows the results of detection of the vaccinia virus. As shown in FIG. 12C, tissues shown in the upper part of the figure are normal tissues, and tissues shown in the lower part of the figure are tumor tissues. *Renilla* luciferase and vaccinia viruses were detected selectively in tumor cells. While activation of the Ras/Raf/MEK/ERK metabolic pathway was observed in such tumor cells, this pathway was not activated in normal cells in the vicinity of the tumor cells.

Figure 13A:
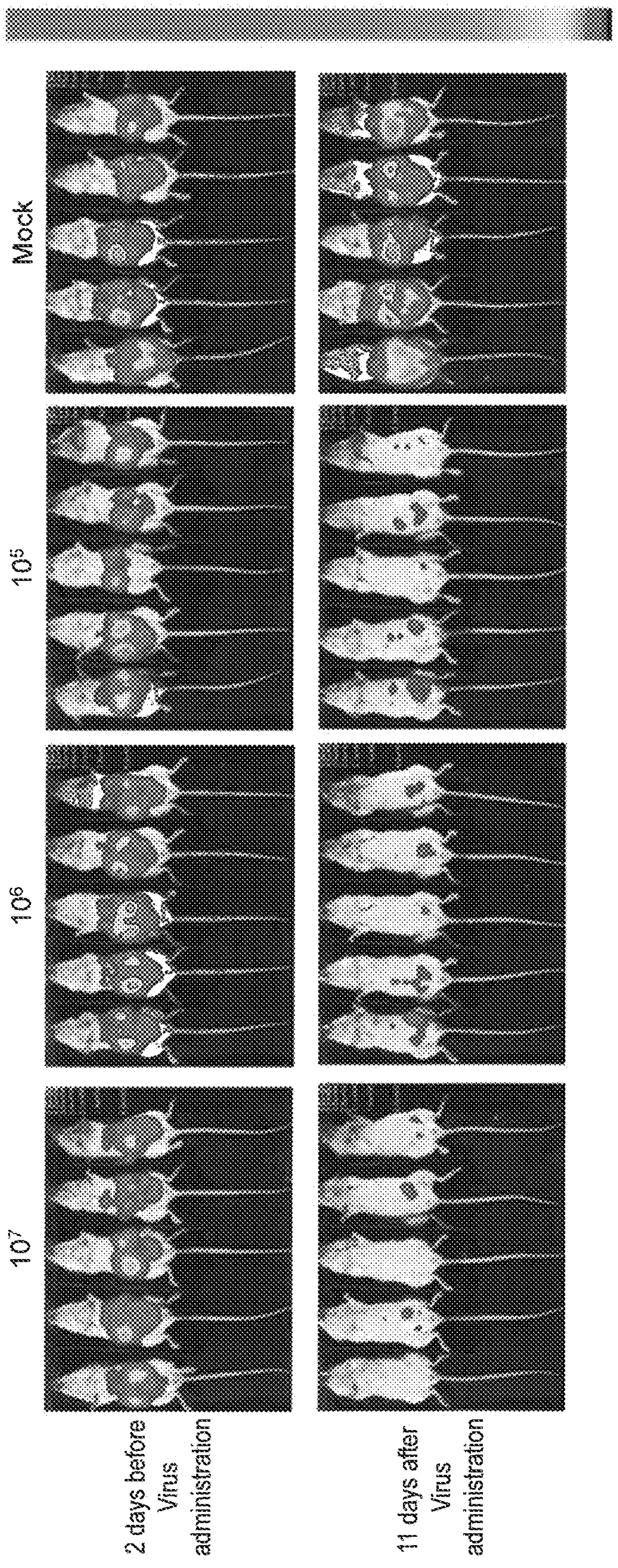
FIG. 13A shows the correlation of a virus dose and anticancer effects in the mouse model for peritoneal dissemination of BxPC-3.
Figure 13B:
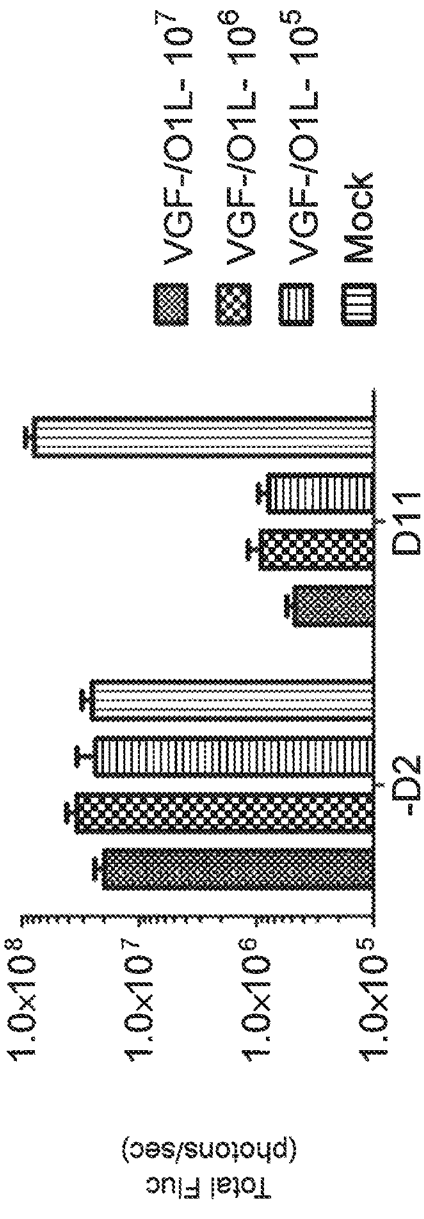
FIG. 13B shows the results of quantification of the correlation of a virus dose and anticancer effects in the mouse model for peritoneal dissemination of BxPC-3.

Example 5: Examination of the Correlation Between the Virus Dose in Mouse Models for Peritoneal Dissemination of BxPC-3 and Anti-Cancer Effects and/or Safety The correlation between the virus dose and anti-cancer effects/safety was evaluated using mouse models similar to those used for peritoneal dissemination of BxPC-30 Human pancreatic cancer BxPC3 cells ($5\times10^6$ cells) stably expressing *Renilla* luciferase were administered intraperitoneally to SCID mice, and mitogen-activated protein kinase-dependent recombinant vaccinia virus strains ($10^5$, $10^6$, or $10^7$ pfu) were administered intraperitoneally 7 days thereafter (with each group consisting of 5 mice). Coelenterazine, which is a *Renilla* luciferase substrate, was administered intraperitoneally 2 days before virus administration and 11 days after virus administration, the tumor cells (i.e., the number of grown cells) in the mouse body were subjected to non-invasive observation using the in vivo imaging system (Berthold, NightDHADE LB985) (FIG. 13A), and the results of observation were quantified (FIG. 13B). As a result, equivalent levels of peritoneal dissemination of BxPC-3 cells were observed without significant difference among all groups 2 days before virus administration, and 87.7% to 98.3% of the tumor cells, 92.4% to 99.3% of the tumor cells, and 88.3% to 98.9% of the tumor cells that had existed before treatment had disappeared from the abdominal cavities of the mice to which $10^5$ pfu, $10^6$ pfu, and $10^7$ pfu of viruses had been administered, respectively, 11 days after the initiation of treatment. Such disappearance of tumors was observed at equivalent levels among these groups. In the control group, in contrast, no therapeutic effects were observed, and the growth of tumors was observed. Virus types (i.e., mO strains (mO), VGF-deficient mO strains (VGF−), O1L-deficient mO strains (O1L−), and VGF−/O1L-deficient mO strains (VGF−/O1L−)) are indicated on top of the images in FIG. 13A and on the right side of the bars in FIG. 13B. In FIG. 13A, the bar shown on the right side of images indicates the luminous intensity of a light source induced by luciferase (i.e., the power of light) in the order of red, orange, yellow, greenish yellow, blue, and purple from the top to the bottom. In FIG. 13B, the total number of photons/sec, which is the unit indicating the light intensity, is indicated on the vertical axis.

Figure 14:
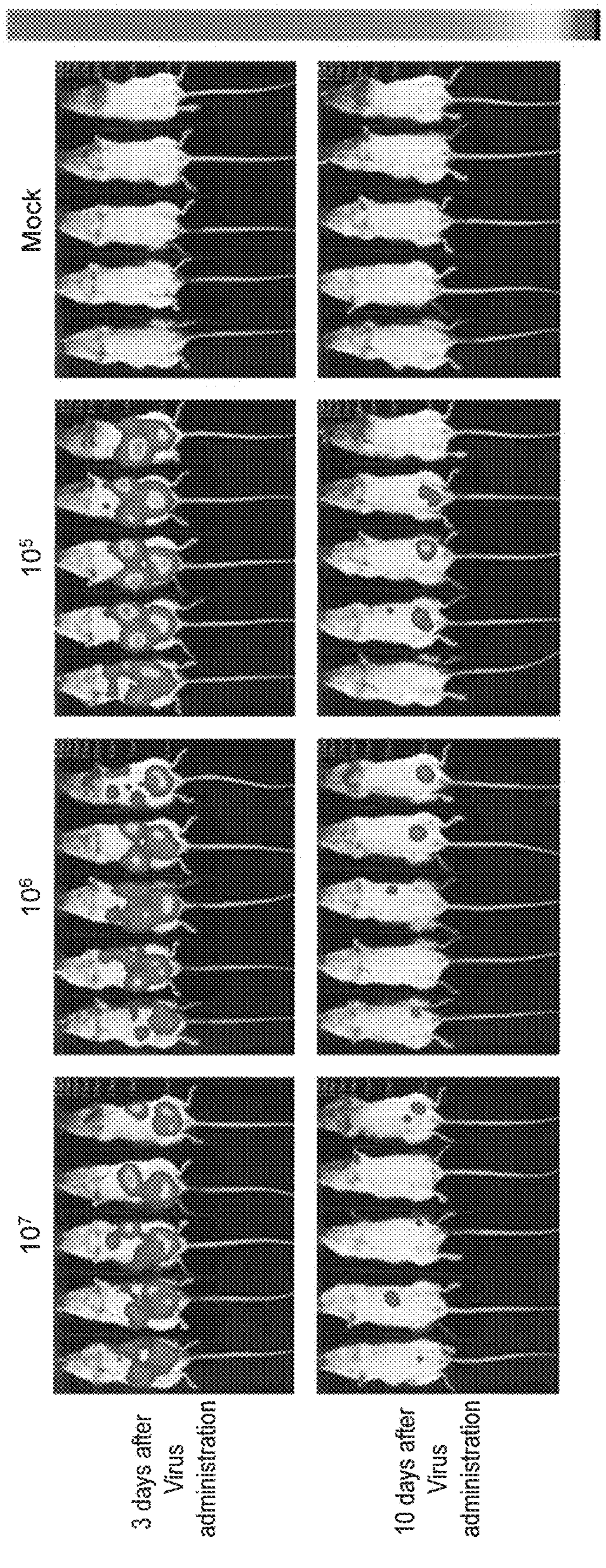
FIG. 14 shows the correlation of a virus dose and safety in the mouse model for peritoneal dissemination of BxPC-3.

Subsequently, luciferin, which is a firefly luciferase substrate, was administered intraperitoneally 3 days and 10 days after virus administration, and the virus distribution in the mouse body was observed in a non-invasive manner. As a result, 3 days after administration, the growth of viruses was observed in tumors in the abdominal cavity at equivalent levels among the groups of mice to which viruses ($10^5$, $10^6$, or $10^7$ pfu of VGF−/O1L−) had been administered. The viruses had disappeared from the body, or the growth of viruses had been restricted to tumors in the abdominal cavity (that is, the growth of viruses was not observed in normal tissues) 10 days after administration (FIG. 14). Virus types (i.e., mO strains (mO), VGF-deficient mO strains (VGF−), O1L-deficient mO strains (O1L−), and VGF−/O1L-deficient mO strains (VGF−/O1L−)) are indicated on top of the images in FIG. 14.

As described above, the growth capacity of the mitogen-activated protein kinase-dependent recombinant vaccinia virus strain (VGF−/O1L−) is significantly lowered in normal cells in which the Ras/Raf/MEK/ERK metabolic pathway is not activated. In tumor cells in which the Ras/Raf/MEK/ERK metabolic pathway is activated, in contrast, the functions of the VGF−/O1L− virus strains for ERK activation would be complemented, and viruses could grow, which was verified in the mouse body. In addition, the anti-cancer effects observed in the group subjected to treatment with VGF−/O1L− were equivalent to those observed in the group subjected to treatment with the 10-fold dose and the 100-fold dose of VGF−/O1L−. That is, an advantage in terms of virotheapy such that virus-infected tumor cells are killed while viruses keep growing therein can be achieved with smaller doses of viruses.

INDUSTRIAL APPLICABILITY

The mitogen-activated protein kinase-dependent recombinant vaccinia virus strain according to the present invention lacks functions of VGF and O1L that activate the Ras/Raf/MEK/ERK metabolic pathway, in normal cells, the Ras/Raf/MEK/ERK metabolic pathway cannot be activated, the cells do not grow, and, accordingly, vaccinia viruses cannot grow. That is, normal cells would not be damaged, in cancer cells, however, the Ras/Raf/MEK/ERK metabolic pathway has already been activated to an abnormal extent. Thus, cancer cells can grow even if the pathway is not activated by VGF and O1L. Therefore, the mitogen-activated protein kinase-dependent recombinant vaccinia virus strain of the present invention can be used for the treatment of cancer.

In addition, the vaccinia virus is characterized by its wide host range and a high degree of expression efficiency. Thus, it can also function as a vector that introduces another foreign gene. The mitogen-activated protein kinase-dependent recombinant vaccinia viruses expressing luciferase or GFP enable simple and rapid identification of cells that have been infected with the viruses. Also, a therapeutic gene having cytotoxic effects or immunostimulating effects may be expressed and used in combination with other therapeutic techniques.

Sequence Listing Free Text

SEQ ID NOs: 3 to 8 and 13 to 22: Primers

SEQ ID NOs: 9 to 12: Synthetic DNAs

All publications, patents, and patent applications cited herein are incorporated herein by reference in their entirety.

The invention claimed is:

1. A mitogen-activated protein kinase-dependent vaccinia virus, which is deprived of functions of the vaccinia virus growth factor (VGF) and O1L, which does not grow in a normal cell but grows specifically in a cancer cell, and which has oncolytic properties of specifically damaging cancer cells.

2. The mitogen-activated protein kinase-dependent vaccinia virus according to claim 1, wherein the vaccinia virus is the LC16 strain, the LC16mO strain, or the LC16m8 strain modified to express the B5R gene.

3. A pharmaceutical composition used in treatment of cancer comprising the vaccinia virus according to claim 1.

4. A mitogen-activated protein kinase-dependent vaccinia virus vector comprising foreign DNA introduced into the mitogen-activated protein kinase-dependent vaccinia virus according to claim 1.

5. The mitogen-activated protein kinase-dependent vaccinia virus vector according to claim 4, wherein the foreign DNA is marker DNA, a therapeutic gene having cytotoxic effects or immunostimulating effects, or DNA encoding a cancer, virus, bacterium, or protozoan antigen.

6. A pharmaceutical composition comprising the mitogen-activated protein kinase-dependent vaccinia virus vector according to claim 4, which is used in treatment of cancer or used as a vaccine against cancer, viruses, bacteria, or protozoa.

7. A pharmaceutical composition used in treatment of cancer comprising the vaccinia virus according to claim 2.

8. A mitogen-activated protein kinase-dependent vaccinia virus vector comprising foreign DNA introduced into the mitogen-activated protein kinase-dependent vaccinia virus according to claim 2.

9. A pharmaceutical composition comprising the mitogen-activated protein kinase-dependent vaccinia virus vector according to claim 5, which is used in treatment of cancer or used as a vaccine against cancer, viruses, bacteria, or protozoa.

* * * * *

SEQUENCE LISTING

```
<160> NUMBER OF SEQ ID NOS: 22

<210> SEQ ID NO 1
<211> LENGTH: 423
<212> TYPE: DNA
<213> ORGANISM: Vaccinia virus

<400> SEQUENCE: 1

atgttgataa attatctgat gttgttgttc gctgctatga taatcagatc attcgccgat     60

agtggtaacg ctatcgaaac gacattgcca gaaattacaa acgctacaac agatattcca    120

gctatcagat tatgcggtcc agagggagat ggatattgtt tacacggtga ctgtatccac    180

gctagagata ttgacggtat gtattgtaga tgctctcatg gttatacagg cattagatgt    240

cagcatgtag tattagtaga ctatcaacgt tcagaaaacc caaacactac aacgtcatat    300

atcccatctc ccggtattat gcttgtatta gtaggcatta ttattattac gtgttgtcta    360

ttatctgttt ataggttcac tcgacgaact aaactactta tacaagatat ggttgtgcca    420

taa                                                                  423

<210> SEQ ID NO 2
<211> LENGTH: 2001
<212> TYPE: DNA
<213> ORGANISM: Vaccinia virus

<400> SEQUENCE: 2

atgttcatgt atccggaatt tgcgaggaag gctttatcaa agcttatttc aaaaaaatta     60

aacattgaaa aggtgtctag caagcaccag ctcgtgttac tggattatgg attacacgga    120

ctattgccaa aatcactgta tctggaagct attaactccg acattctcaa tgttaggttt    180

tttcctcctg aaataataaa cgtcactgat atcgttaagg ctctccaaaa ttcttgtaga    240

gtagatgagt acctaaaagc tgtttcctta tatcataaga attctttaat ggtatcggga    300
```

-continued

```
ccaaatgtag tcaagcttat gatagaatat aatcttctta cacacagtga cttggaatgg    360
ttaattaatg agaatgtagt caaggctaca taccttttaa aaatcaatgc ctatatgatt    420
aactttaaaa tagatctaac ggttgatgaa atcattgact tagttaaaga tattcctgta    480
ggagctacgc tacatctata taatatatta aacaatatag atttggacat tgttcttcgt    540
atatctgatg aatataatat accacctgtt cacgatattc tgtctaaact taccgatgaa    600
gagatgtgta taaaactagt tacaaagtat cctatggaca atgttataaa ttttattaat    660
caagatgtta gatatagtcc caccttcatc aagacaatta aagattttgt caacaagcat    720
cttccaacca tgtacgatgg attaaatgat tatctacatt ctgttattat cgacgaggac    780
ttaatagagg aatataaaat taaatccgtt gccatgttta atttggaata caaaactgat    840
gtaaatactc taacattgga cgaacagata tttgtagagg taaacatctc atattatgat    900
tttagatata gacaatttgc cgatgaattt agagattaca ttatgataaa agaaagaaga    960
caaatcacca tgcaatctgg tgatagaata agaaggttta gacgtcccat gtcattgaga   1020
tccactatca tcaaaaagga tactgattct ctagaggata ttctcgcaca tatagataat   1080
gccagaaaaa atagcaaggt atccattgaa gatgttgaga gaatcatttc atctttccgt   1140
cttaatccct gtgttgtcag acgcaccatg ctgtctgata tagatatcaa aacaaagata   1200
atggtgctaa aaattgtcaa agattggaaa tcttgtgctc tgacactatc agccatcaaa   1260
ggaattatgg taacagatac catcaatacc gtgttatcca aaattctgca tcatcatagg   1320
aatgtcttca agtatcttac atctgtagag aataaagaaa ttgctgtctg taattgctcc   1380
agatgtctgt cgctcttcta tagagaatta aaaagtgtac gatgtgatct acacacagac   1440
gatggattat tggataggct atacgatctg actagatacg ccttacacgg aaaaatcaat   1500
caaaacttaa tcggtcaacg atgttggggt ccgttgacag aaatgctgtt taacgagaat   1560
aaaaagaaaa aactaaataa tttaatggaa tacatcaaaa tatcagacat gttggtatac   1620
ggacactcta tcgagaagac gcttattcca attactgatt ctctttcatt caagctatct   1680
gttgatacca tgtctgtgtt aaatgatcaa tatgccaagg ttgtcatctt cttcaatacc   1740
atcatagaat atattatagc tactatctat tatagattga cagtcttgga caattatact   1800
aatgtcaaac attttgtatc caaagtgtta cacactgtca tggaagcatg tggcgtactg   1860
ttttcataca ttaaagttaa tgacaaaata gagcatgaat tggaggagat ggtggacaaa   1920
ggtaccgtac cttcttattt gtatcatctg tccatcaacg tcatttcaat aatattggat   1980
gatataaatg gaactcgtta a                                             2001
```

```
<210> SEQ ID NO 3
<211> LENGTH: 29
<212> TYPE: DNA
<213> ORGANISM: Artificial
<220> FEATURE:
<223> OTHER INFORMATION: Primer

<400> SEQUENCE: 3

cgcggatcct attctcattc atattctct                                       29


<210> SEQ ID NO 4
<211> LENGTH: 32
<212> TYPE: DNA
<213> ORGANISM: Artificial
<220> FEATURE:
<223> OTHER INFORMATION: Primer

<400> SEQUENCE: 4
```

cgcaagctta gatctggaaa atgtctgtta gt 32

<210> SEQ ID NO 5
<211> LENGTH: 28
<212> TYPE: DNA
<213> ORGANISM: Artificial
<220> FEATURE:
<223> OTHER INFORMATION: Primer

<400> SEQUENCE: 5
gcgctagctt aacgagttcc atttatat 28

<210> SEQ ID NO 6
<211> LENGTH: 29
<212> TYPE: DNA
<213> ORGANISM: Artificial
<220> FEATURE:
<223> OTHER INFORMATION: Primer

<400> SEQUENCE: 6
gcgctagcat gttcatgtat ccggaattt 29

<210> SEQ ID NO 7
<211> LENGTH: 29
<212> TYPE: DNA
<213> ORGANISM: Artificial
<220> FEATURE:
<223> OTHER INFORMATION: Primer

<400> SEQUENCE: 7
cgcagctgag cttttgcgat caataaatg 29

<210> SEQ ID NO 8
<211> LENGTH: 23
<212> TYPE: DNA
<213> ORGANISM: Artificial
<220> FEATURE:
<223> OTHER INFORMATION: Primer

<400> SEQUENCE: 8
ttcagctgaa tatgaaggag caa 23

<210> SEQ ID NO 9
<211> LENGTH: 42
<212> TYPE: DNA
<213> ORGANISM: Artificial
<220> FEATURE:
<223> OTHER INFORMATION: Synthetic

<400> SEQUENCE: 9
aattgcatgc gtcgacatta atggccggac cggccttcga ag 42

<210> SEQ ID NO 10
<211> LENGTH: 42
<212> TYPE: DNA
<213> ORGANISM: Artificial
<220> FEATURE:
<223> OTHER INFORMATION: Synthetic

<400> SEQUENCE: 10
aattcttcga aggccggtcc ggccattaat gtcgacgcat gc 42

<210> SEQ ID NO 11
<211> LENGTH: 99
<212> TYPE: DNA

<213> ORGANISM: Artificial
<220> FEATURE:
<223> OTHER INFORMATION: Synthetic

<400> SEQUENCE: 11
tcgaaattgg atcagctttt tttttttttt ttttggcata taaataaggt cgaggtacca 60
aaaattgaaa aactattcta atttattgca cggccggac 99

<210> SEQ ID NO 12
<211> LENGTH: 92
<212> TYPE: DNA
<213> ORGANISM: Artificial
<220> FEATURE:
<223> OTHER INFORMATION: Synthetic

<400> SEQUENCE: 12
cggccgtgca ataaattaga atagtttttc aatttttggt acctcgacct tatttatatg 60
ccaaaaaaaa aaaaaaaaaa gctgatccaa tt 92

<210> SEQ ID NO 13
<211> LENGTH: 30
<212> TYPE: DNA
<213> ORGANISM: Artificial
<220> FEATURE:
<223> OTHER INFORMATION: Primer

<400> SEQUENCE: 13
caacccgggc catggaagat gccaaaaaca 30

<210> SEQ ID NO 14
<211> LENGTH: 30
<212> TYPE: DNA
<213> ORGANISM: Artificial
<220> FEATURE:
<223> OTHER INFORMATION: Primer

<400> SEQUENCE: 14
ctgcggccgc cacggcgatc ttgccgccct 30

<210> SEQ ID NO 15
<211> LENGTH: 37
<212> TYPE: DNA
<213> ORGANISM: Artificial
<220> FEATURE:
<223> OTHER INFORMATION: Primer

<400> SEQUENCE: 15
gcgcggccgc agccaccatg gtgagcaagg gcgagga 37

<210> SEQ ID NO 16
<211> LENGTH: 40
<212> TYPE: DNA
<213> ORGANISM: Artificial
<220> FEATURE:
<223> OTHER INFORMATION: Primer

<400> SEQUENCE: 16
gctgcggccg cttcgaattc ttacttgtac agctcgtcca 40

<210> SEQ ID NO 17
<211> LENGTH: 19
<212> TYPE: DNA
<213> ORGANISM: Artificial
<220> FEATURE:
<223> OTHER INFORMATION: Primer -continued

<400> SEQUENCE: 17
atgttgataa attatctga 19

<210> SEQ ID NO 18
<211> LENGTH: 19
<212> TYPE: DNA
<213> ORGANISM: Artificial
<220> FEATURE:
<223> OTHER INFORMATION: Primer

<400> SEQUENCE: 18
ttatggcaca accatatct 19

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
acagggatta agacggaaag 20

<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
gtcaacaagc atcttccaac 20

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
cgactataga cataatacta 20

<210> SEQ ID NO 22
<211> LENGTH: 20
<212> TYPE: DNA
<213> ORGANISM: Artificial
<220> FEATURE:
<223> OTHER INFORMATION: Primer

<400> SEQUENCE: 22
cagatgatgc acttactgta 20